(12) United States Patent
Rasor et al.

(10) Patent No.: US 6,959,708 B1
(45) Date of Patent: Nov. 1, 2005

(54) METHOD FOR CO-APPLICATION OF GASES AND DRUGS TO POTENTIATE THEIR ACTION IN RELIEVING HEADACHES, ANGINA AND OTHER AILMENTS

(75) Inventors: Ned S. Rasor, Cupertino, CA (US); Julia S. Rasor, Los Gatos, CA (US)

(73) Assignee: Capnia, Incorporated, Mountain View, CA (US)

( * ) Notice: Subject to any disclaimer, the term of this patent is extended or adjusted under 35 U.S.C. 154(b) by 485 days.

(21) Appl. No.: 09/708,186

(22) Filed: Nov. 7, 2000

Related U.S. Application Data

(60) Provisional application No. 60/185,495, filed on Feb. 28, 2000, provisional application No. 60/164,125, filed on Nov. 8, 1999.

(51) Int. Cl.[7] ............................................. A61M 16/10
(52) U.S. Cl. ............ 128/203.12; 128/898; 128/200.24; 604/19; 604/24; 604/26
(58) Field of Search ....................... 128/200.14–200.24, 128/203.12, 204.18, 207.14–207.18, 203.15, 128/898, 203.14, 203.18, 203.21, 203.23; 604/19–26

(56) References Cited

U.S. PATENT DOCUMENTS

| | | | |
|---|---|---|---|
| 1,449,047 A | | 3/1923 | Johnson |
| 2,651,303 A | | 9/1953 | Johnson et al. |
| 2,920,623 A | | 1/1960 | Holt |
| 3,425,414 A | | 2/1969 | Roche |
| 3,513,843 A | | 5/1970 | Exler |
| 3,776,227 A | | 12/1973 | Pitesky et al. |
| 3,934,585 A | | 1/1976 | Maurice |
| 3,974,830 A | * | 8/1976 | LaVerne ................. 128/203.27 |
| 4,067,499 A | | 1/1978 | Cohen |
| 4,137,914 A | | 2/1979 | Wetterlin |
| 4,188,946 A | | 2/1980 | Watson et al. |
| 4,447,449 A | * | 5/1984 | Marshall ...................... 514/456 |
| 4,554,916 A | | 11/1985 | Watt |
| 5,099,834 A | | 3/1992 | Fishman |
| 5,262,180 A | | 11/1993 | Orlando et al. |
| 5,318,015 A | | 6/1994 | Mansson et al. |
| 5,370,862 A | * | 12/1994 | Klokkers-Bethke et al. .. 424/47 |
| 5,431,155 A | | 7/1995 | Marelli |
| 5,485,827 A | * | 1/1996 | Zapol et al. ........... 128/200.14 |

(Continued)

FOREIGN PATENT DOCUMENTS

CH   247 873 A   3/1947

(Continued)

OTHER PUBLICATIONS

Hummel, et al., "Comparison of the antinociception produced by two oral formulations of ibuprofen; ibuprofen effervescent vs ibuprofin tablets," Eur J Clin Pharmacol (1997) 52: 107-114.

(Continued)

Primary Examiner—Glenn K. Dawson
(74) Attorney, Agent, or Firm—Townsend and Townsend and Crew LLP

(57) ABSTRACT

Apparatus, methods and kits for treating symptoms associated with common ailments such as headaches, rhinitis, asthma, epilepsy, nervous disorders and the like, are provided. The apparatus includes dispensers for carbon dioxide and other therapeutic gases. The methods include delivering small volumes of these gases to patients in a manner where the gas infuses a body region in order to bathe the mucous membranes therein. It has been found that even very short exposure of patients to small volumes and high concentrations of such gases can provide significant relief from symptoms.

24 Claims, 23 Drawing Sheets

U.S. PATENT DOCUMENTS

| | | | |
|---|---|---|---|
| 5,490,498 | A | 2/1996 | Faithfull et al. |
| 5,558,083 | A | 9/1996 | Bathe et al. |
| 5,570,683 | A | 11/1996 | Zapol |
| 5,807,357 | A | 9/1998 | Kang |
| 5,839,433 | A * | 11/1998 | Higenbottam .......... 128/204.21 |
| 5,851,544 | A | 12/1998 | Penska et al. |
| 5,875,776 | A | 3/1999 | Vaghefi |
| 5,891,885 | A * | 4/1999 | Caruso ....................... 514/289 |
| 5,918,596 | A | 7/1999 | Heinonen |
| 5,941,241 | A | 8/1999 | Weinstein et al. |
| 5,951,538 | A | 9/1999 | Joshi et al. |
| 6,001,332 | A * | 12/1999 | Garrett ........................ 424/9.3 |
| 6,125,844 | A * | 10/2000 | Samiotes ............... 128/200.23 |
| 6,258,032 | B1 * | 7/2001 | Hammesfahr ............... 600/454 |

FOREIGN PATENT DOCUMENTS

| | | |
|---|---|---|
| DE | 837 158 C | 4/1952 |
| DE | 14 91 660 A | 8/1969 |
| DE | 89 06 590 U | 10/1989 |
| EP | 0 768 094 A | 4/1997 |
| FR | 2656218 A1 | 12/1989 |
| GB | 408 856 A | 4/1934 |
| WO | WO 91 08793 | 6/1991 |
| WO | WO 93 00951 A | 1/1993 |
| WO | WO 00/51672 | 9/2000 |

OTHER PUBLICATIONS

Lipkin, et al., "Migraine and Sudden Sensorineural Hearing Loss," Arch Otolarynhol Head Neck Surg (1987) 113: 325-26.

Tang, et al., "Effect of CO2 on serotonin-induced contraction of isolated smooth muscle," Clin Research (1972) 20: 243.

Qi, et al., "An experiment study of reversed plumonary hypertension with inhaled nitric oxide on smoke inhaltion injury," Chung Hua Wai Ko Tsa Chih (Jan. 1997) 35(1): 56-58.

Loh, et al., "Cardiovascular effects of inhaled nitric oxide in a canine model of cardiomyopathy," Ann Thorac Surg (May 1999) 67(5): 1380-5.

Pagano, et al., "A comparison of inhaled nitric oxide with intravenous vasodilators in the assessment of pulmonary haemodynamics prior to cardiac transplantation," Eur J Cardiothorac Surg (1996) 10(12): 1120-26.

Declaration by Ned Rasor regarding use of invention prior to filing.

Mischler, SA; Alexander, M.; Battles, AH; Raucci, JA; Nalwalk, JW; Hough, LB: Prolonged Antinociception Following Carbon Dioxide Anesthesia in the Labroatory Rat. Brain Research, 640 (1994) 322-327.

Gronross, M.; Pertovaara, A.: A Selective Suppression of Human Pain Sensitivity by Carbon Dioxide: Central Mechanisms Implicated. Eur J Appl Physiol (1994) 68: 74-79.

Schaeffer, E.; Pohlman, A.; Morgan, S.; Hall, JB: Oxygenation in Status Asthmaticus Improves During Ventilation with Helium-Oxygen, Crit Car Med (1999) vol. 27, No. 12, pp. 2666-2670.

Faisy, C.; Diehl, L.; Guerot, E; Rezgui, N.; Labrousese, J.: Utilisation du Melange Helium-Oxygene En Practique Pneumologique. Rev Mal Respir (1999) 16, 1063-1073.

Marcussen, R.; Wolff, H.: Studies on Headache. Archives of Neurology & Psychiatry, vol. 63 (1950) pp. 43-51.

Shunzheng, Q.; Zongchen, Y.; Baobin, H.: An Experiment Study of Reversed Pulmonary Hypertension with Inhaled Nitric Oxide on Smoke Inhalation Injury. Chin J. Surg, Jan (1996) vol. 35, No. 1, pp. 56-58.

La Verne, A: "Rapid Coma Technic of Carbon Dioxide Therapy" In *Carbon Dioxide Therapy, A Neurophysiological Treatment of Nervous Disorders,* Medina, LJ ed., Charles C Thomes, Springfield, Inninois, pp 269-293.

* cited by examiner

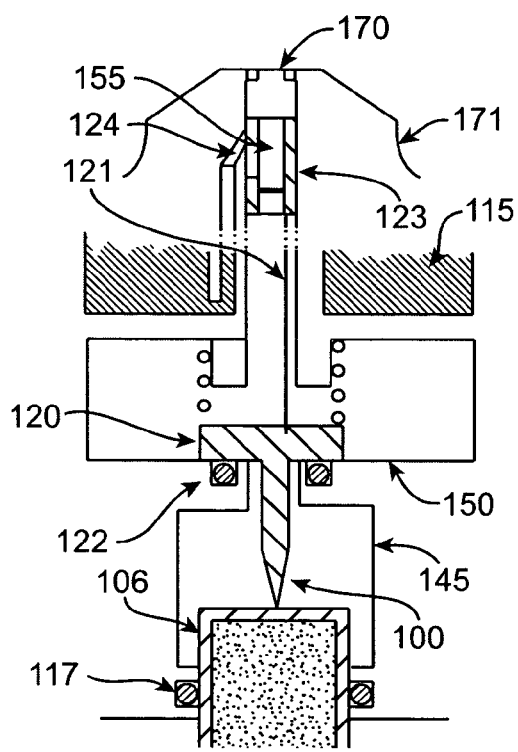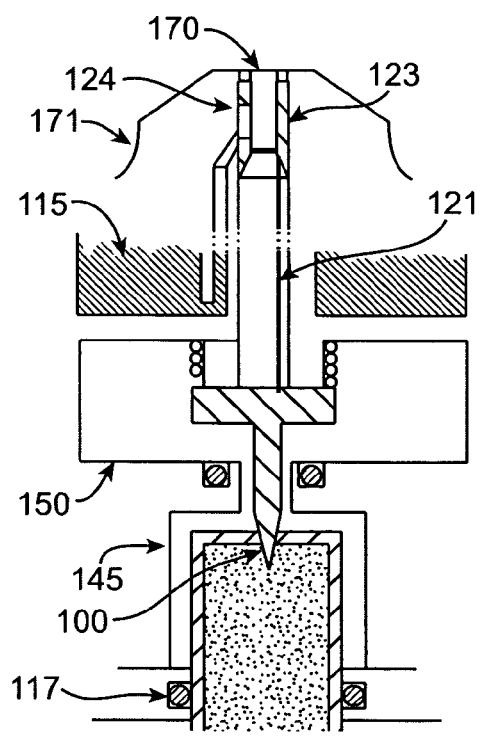
FIG. 5a  FIG. 5b
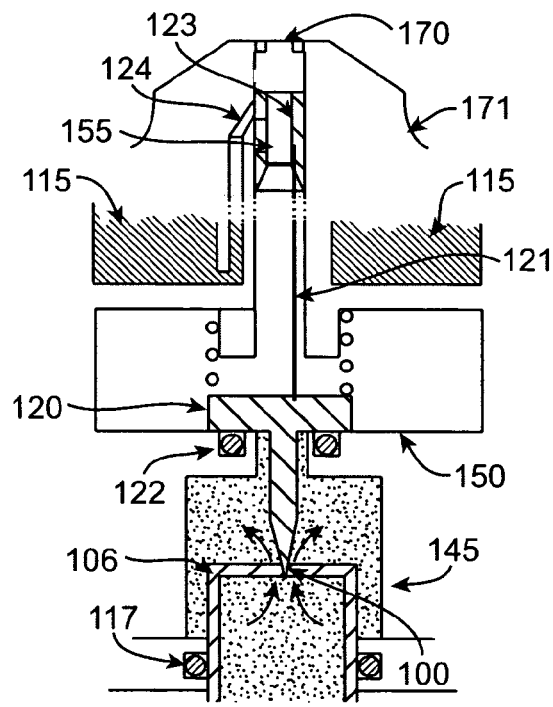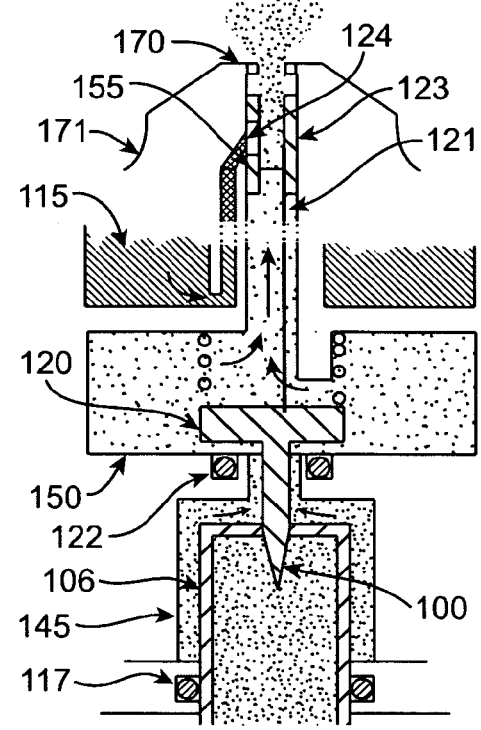
FIG. 5c  FIG. 5d $\tan \alpha/2 \sim \alpha/2 = d/x$
$d \sim \alpha x/2$
$\alpha \sim 2\, d/x\ \ 115\, d/x\ \text{deg}$

METHOD FOR CO-APPLICATION OF GASES AND DRUGS TO POTENTIATE THEIR ACTION IN RELIEVING HEADACHES, ANGINA AND OTHER AILMENTS

CROSS-REFERENCE TO RELATED APPLICATIONS

This application claims the benefit of U.S. Provisional Patent Application No. 60/164,125, filed on Nov. 8, 1999 and 60/185,495, filed on Feb. 28, 2000 each of which is incorporated by reference herein.

BACKGROUND OF THE INVENTION

1. Field of the Invention

This invention relates to gas dispensers and methods for delivering carbon dioxide ($CO_2$), or other gas to individuals. Similar methods and devices are described in U.S. patent application Ser. No. 09/614,389 filed Jul. 12, 2000, which is incorporated by reference herein. That application describes use of $CO_2$, or other therapeutic gas or agents, and associated transmucosal dispensing apparatus for providing controlled amounts of gas to the nose, mouth and/or eye for use in the relief of headaches, allergic rhinitis and asthma, among other ailments. The present invention, however, includes methods and transmucosal or inhalational dispensing apparatus for co-application of selected drugs with gas and/or vapor to potentiate (i.e., beneficially improve) the action of the drug or of the gas or vapor.

One possible physiological basis for the invention is as follows:

Drugs act upon blood vessels (vasoactive drugs), muscles (myoactive drugs), and/or nerves (neuroactive drugs) to produce their beneficial effects. It is well established that vasoactive drugs (causing vasodilation or vasoconstriction) may be used to relieve allergic rhinitis (e.g., vasocontrictor decongestants) as well as migraine and other forms of headache (e.g., vasoconstrictors). Similarly, myoactive drugs that cause bronchial smooth muscle relaxation result in bronchodilation and increased ventilation. It is also well established that myoactive drugs (causing muscle contraction or muscle relaxation) and neuroactive drugs (causing neural excitation or neural inhibition) may be used to relieve asthma (sympathomimetic bronchodilators).

Like drugs, certain gases and vapors are physiologically active substances. The gases carbon dioxide and nitric oxide are known to be vasoactive, myoactive, and neuroactive [1]. Oxygen, nitrous oxide, helium, and dilute mixtures of nitric oxide may also be vasoactive, myoactive, and/or neuroactive. In addition, vapors from certain substances that lower the pH of mucosa to a degree similar to that of carbon dioxide, such as hydrochloric acid (HCl), nitric acid ($HNO_3$), and hydrofluoric acid (HF) (all usually diluted with air) can be effective [6], and thus, in general, isocapnic mixtures of acid gases may be effective as well. Therefore, as used herein, "gas" and "gaseous" may refer to any physiologically active gas or vapor.

If a drug is co-applied to a particular tissue or organ with $CO_2$, NO, or other vasoactive, myoactive, or neuroactive gas or vapor as taught and claimed herein, the speed and efficacy of the drug action in such tissue or organ may be controlled. As a specific example for $CO_2$, in an in vivo test, the ability of the drug atropine to inhibit serotonin-induced bronchial smooth muscle contraction was found to be potentiated from 46% inhibition to 62% inhibition by co-application of a 10% $CO_2$ concentration [2]. Similarly, the inhibitory effect of the drug hexamethonium was potentiated from 37% inhibition to 67% inhibition by co-application of a 10% $CO_2$ [2].

The co-application of a drug with a gas or vapor can be performed in at least three different ways: First, the drug and gas can be applied together locally by co-infusion and transmucosal co-absorption nasally, orally, and/or via the eye or ear. The form of the drug, of course, would need to be suitable for such infusion, for example, a fine powder or liquid. If the combination of the drug and gas is applied nasally or orally for local transmucosal absorption, the individual would substantially inhibit passage of the drug and gas into his lungs and trachea by limiting inhalation of the gas and drug. Second, the drug and gas may be applied separately. The drug may be applied by any conventional means such as inhalation, pills, capsules, hypodermic injection or epidermal patches, and the individual may infuse a nostril or nostrils, mouth, eye or ear with the gas before, during or after application of the drug. As a variation of this method of co-application, the gas may instead be inhaled. Third, a combination of the drug and gas may be inhaled.

As an example of the first method, a drug presently infused into the respiratory passages, mouth, eyes, or ears by entraining with air, e.g., as an aerosol, powder, or spray, can be applied instead by entraining with $CO_2$, e.g., through aspiration of a drug-containing liquid or powder by $CO_2$. In particular, the action of drugs developed and presently used for relieving respiratory and headache symptoms may be improved by their co-infusion with $CO_2$ or NO. The vasodilation induced by $CO_2$ or NO improves the speed and extent of absorption and distribution of the drug in the tissue in which it is co-absorbed with $CO_2$ or NO. This is beneficial through more rapid relief being obtained, and through reduction in the quantity of drug required to obtain the relief. Reduction in the required quantity of drug reduces the cost of treatment per dose and particularly reduces the side effects of such drugs, which are severe restrictions to their present use.

With respect to the second method, a particular benefit of co-application of such drugs with $CO_2$ is that, in addition to the reduction of the total amount of drug required, the effect of the drug can be controlled or "modulated" in the course of its action after application. Inhalation or infusion of $CO_2$ prior to drug application can increase the effectiveness and reduce the required quantity of the drug. Alternatively, inhalation or infusion of $CO_2$ after application of a drug can enhance the effect of the drug at a controlled rate; i.e., if a more rapid or more intense effect of the drug is desired, $CO_2$ can be inhaled or infused at the rate required to obtain the desired degree of enhancement. A particular advantage of such control is that the drug enhancement effect can be abruptly terminated, by ceasing $CO_2$ inhalation or infusion, at the optimum level of beneficial drug effect that minimizes side or overdose effects. Also, since $CO_2$ is rapidly eliminated from the body via the bloodstream and respiration, the enhancement is reversible after $CO_2$ application is ceased, allowing continuous chronic adjustment of the drug effect.

An example of the beneficial regulation of the effect of a powerful drug by $CO_2$ inhalation or infusion is the co-application of $CO_2$ and nitroglycerin for the relief of acute angina and during onset of a heart attack (myocardial infarction). Nitroglycerin is a powerful vasodilator. Ordinarily persons suffering from angina or from symptoms of heart attack place a nitroglycerin tablet under their tongue (transmucosal delivery). If this is not adequate to relieve the symptoms within three minutes, another tablet is similarly ingested. After another three minutes, if relief is not obtained, this process is again repeated. If the symptoms then persist, a person should be taken immediately to a hospital for emergency treatment. Some persons are extremely sensitive to the side effects of nitroglycerin however, including severe blood pressure reduction that can result in dizziness and fainting, especially after ingesting the second tablet, at a time when good judgment and deliberate corrective action are required. A few minutes of delay can be crucial after the onset of a heart attack. With co-application, $CO_2$ can be inhaled or infused after the first tablet to rapidly enhance and sustain its effects, possibly reducing the need for subsequent tablets. The effects of a second tablet of nitroglycerin can be initiated gradually and reversibly with $CO_2$ application to maintain and extend the optimum degree of pain relief without severe blood pressure reduction.

In all three methods cited only one physiologically active gas is used; however, physiologically active gases may be used together, with or without drugs. For example, $CO_2$ has been found to relax both central and peripheral airways in asthmatic adults [3]. Similarly, in both in vivo and clinical tests, inhaled low dose NO has been found to be as effective as sodium nitroprusside and prostacyclin in reducing transpulmonary gradient and pulmonary vascular resistance, and is highly pulmonary vasoselective [6]. NO has also been found to reverse pulmonary hypertension [4,5]. Therefore, NO and $CO_2$ can be co-applied to potentiate their respective actions.

An essential aspect of co-application if control of drug effect is desired is that the $CO_2$, or similar physiologically active gaseous agent must be available for use by the affected person immediately and conveniently at the time the symptoms appear. The hand-held portable dispenser described in U.S. patent application Ser. No. 09/614,389 fulfills this requirement, but does not provide for a high flow rate which may be advantageous when co-application, and particularly inhalation, of a drug and gaseous agent are desired for potentiation. Additionally, the device described in U.S. patent application Ser. No. 09/614,389 does not provide for simultaneously administering the gaseous agent and the drug.

It is therefore an object of the invention to provide a dispenser that allows a flow rate more suitable for co-application of a drug and gaseous physiologically active agent in certain circumstances. It is a further object of the invention to provide a dispenser that allows for simultaneous co-application of a drug and gaseous physiologic agent and adjustment of the dose of the drug relative to the amount of gaseous agent administered. It is a further object of the invention to provide a method for controlling the effect of a drug through the co-application of a physiologically active agent in gaseous or vaporous form.

2. Description of Background Art

Inhalation devices, systems and methods for delivering carbon dioxide and other gases and aerosols to patients, with and without co-delivery of a drug are described in U.S. Pat. Nos. 3,776,227; 3,513,843; 3,974,830; 4,137,914; 4,554,916; 5,262,180; 5,485,827; and 5,570,683. In general, the methods and devices that provide for co-delivery of a drug and carbon dioxide or other gases do not do so for the purpose of potentiation. For example, carbon dioxide may be used simply as a safe propellant as shown in Wetterlin, U.S. Pat. No. 4,137,914. Additionally, in the devices shown, the gas and the drug are usually combined and stored together, which does not allow for adjustment of the amount of gas infused into the body. Such devices are therefore inappropriate for the purpose of controlling the drug's effect by means of the gas.

Additional background art may be found in the following references:

[1] Guyton A C, Hall J E. *Textbook of Medical Physiology.* Ninth Ed., W.B. Saunders Co., Philadelphia, 1996.

[2] Tang A, Rayner M, Nadel J. "Effect of $CO_2$ on serotonin-induced contraction of isolated smooth muscle. *Clin Research* 20:243, 1972.

[3] Qi S, Yang Z, He B. An experiment study of reversed pulmonary hypertension with inhaled nitric oxide on smoke inhalation injury. *Chung Hua Wai Ko Tsa Chih* 35(1):56–8, January 1997.

[4] Loh E, Lankford E B, Polidori D J, Doering-Lubit E B, Hanson C W, Acker M A. Cardiovascular effects of inhaled nitric oxide in a canine model of cardiomyopathy. *Ann Thorac Surg* 67(5):1380–5, May 1999.

[5] Pagano D, Townend J N, Horton R, Smith C, Clutton-Brock T, Bonser R S. A comparison of inhaled nitric oxide with intravenous vasodilators in the assessment of pulmonary haemodynamics prior to cardiac transplantation. *Eur J Cardiothorac Surg* 10(12):1120–6, 1996.

[6] Sterling G, et al. Effect of $CO_2$ and pH on bronchoconstriction caused by serotonin vs. acetylcholine. *J. of Appl. Physiology*, vol. 22, 1972.

SUMMARY OF THE INVENTION

The current invention includes improvements and modifications to the dispenser disclosed in U.S. application Ser. No. 09/614,389 that permit the co-infusion of carbon dioxide or similar physiologically active agents in the form of a gas or vapor, and a drug, resulting in the potentiation of the action of the drug and/or of the physiologically active agent. Dispensers and methods of application particularly suitable for such co-infusion and for inhalation are described. Alternative means for regulating and modifying the flow of gases in the previously described dispenser embodiments are also described herein. Additionally, the present invention includes additional methods that allow for large volume inhalation of the dispensed gas.

Other features and advantages of the current invention will appear from the following description in which the preferred embodiments have been set forth in detail in conjunction with the accompanying drawings.

BRIEF DESCRIPTION OF THE DRAWINGS

FIG. 5A shows the detail of device operation corresponding to FIG. 1.

FIG. 5B shows the detail of device operation corresponding to FIG. 2.

FIG. 5C shows the detail of device operation corresponding to FIG. 3.

FIG. 5D shows the detail of device operation corresponding to FIG. 4.

DETAILED DESCRIPTION OF THE DRAWINGS

Figure 1:
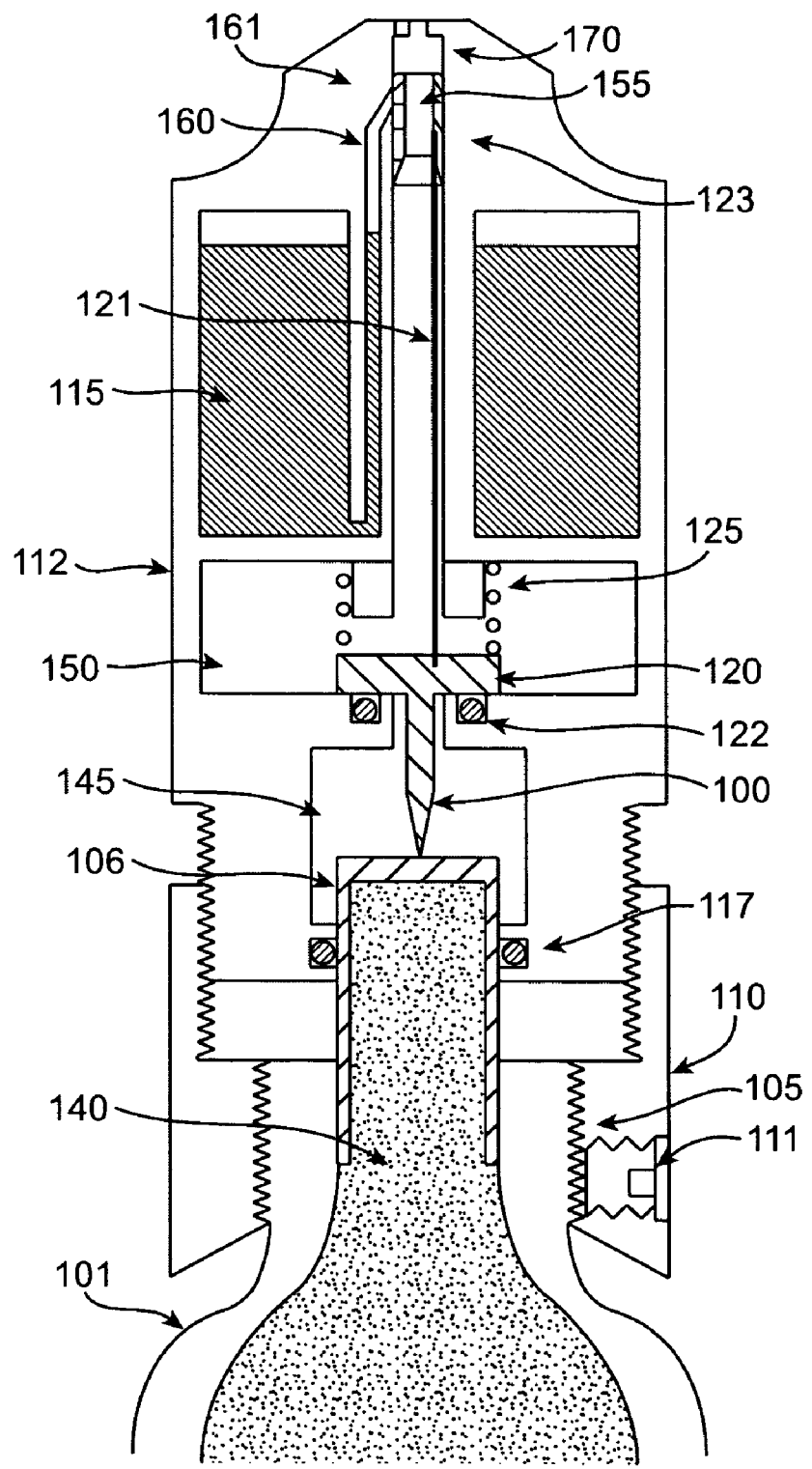
FIG. 1 shows an embodiment of a co-infusion device before it is activated.

Dispenser Means for Co-Infusion of $CO_2$ with Drug

FIGS. 1–7 show a $CO_2$ dispenser embodiment that illustrates a means for the co-infusion of $CO_2$ with drugs. The dispenser embodiment in FIGS. 1–7 is similar to the dispenser embodiments described for $CO_2$ infusion in U.S. patent application Ser. No. 09/614,389. However, in addition to a container of pressurized gas or vapor, a flow regulator, and an outlet, the present invention further includes a container of a quantity of drug-containing liquid or powder agent and a means for mixing and releasing a controlled dose of the drug agent and gas mixture through the outlet at a rate suitable for infusion into a body orifice such as the nose or mouth. Vertical motion in FIGS. 1–5 and related figures is exaggerated to clarify the dispenser action.

The $CO_2$ cartridge 101 in the co-infusion embodiment shown in FIGS. 1–7 has a threaded neck 105 and a cup-shaped sealing cap 106, both of which features have been used in commercial gas cartridge embodiments separately but not necessarily together. In the embodiments shown in FIGS. 1–7 here a collar 110 is screwed onto the $CO_2$ cartridge neck 105. A set screw 111 in the collar 110 prevents movement of the collar 110 relative to the cartridge 101. A rotatable head 112 containing a seal-perforating needle 100, the drug agent 115, and the means for its controlled mixing and ejection with $CO_2$ is screwed into the fixed collar 110 and is sealed to the cartridge sealing cap 106 by an O-ring gasket 117. As a safety feature the diameter of the sealing cap 106 above the location of the O-ring 117 should be less than the inside sealing diameter of the O-ring 117 so that any high pressure gas in the plenum 150 will be controllably released before the collar and head can be completely unscrewed and separated.

As shown in FIG. 1, the device is marketed with the sealing cap 106 intact. The rotatable head 112 is screwed into the fixed collar 110 only partially such that the perforating needle 100 does not penetrate the sealing cap 106. The sequence of operation of the co-dispenser shown in FIGS. 1–4 is shown in enlarged detail in FIGS. 5*a*–5*d*.

Figure 2:
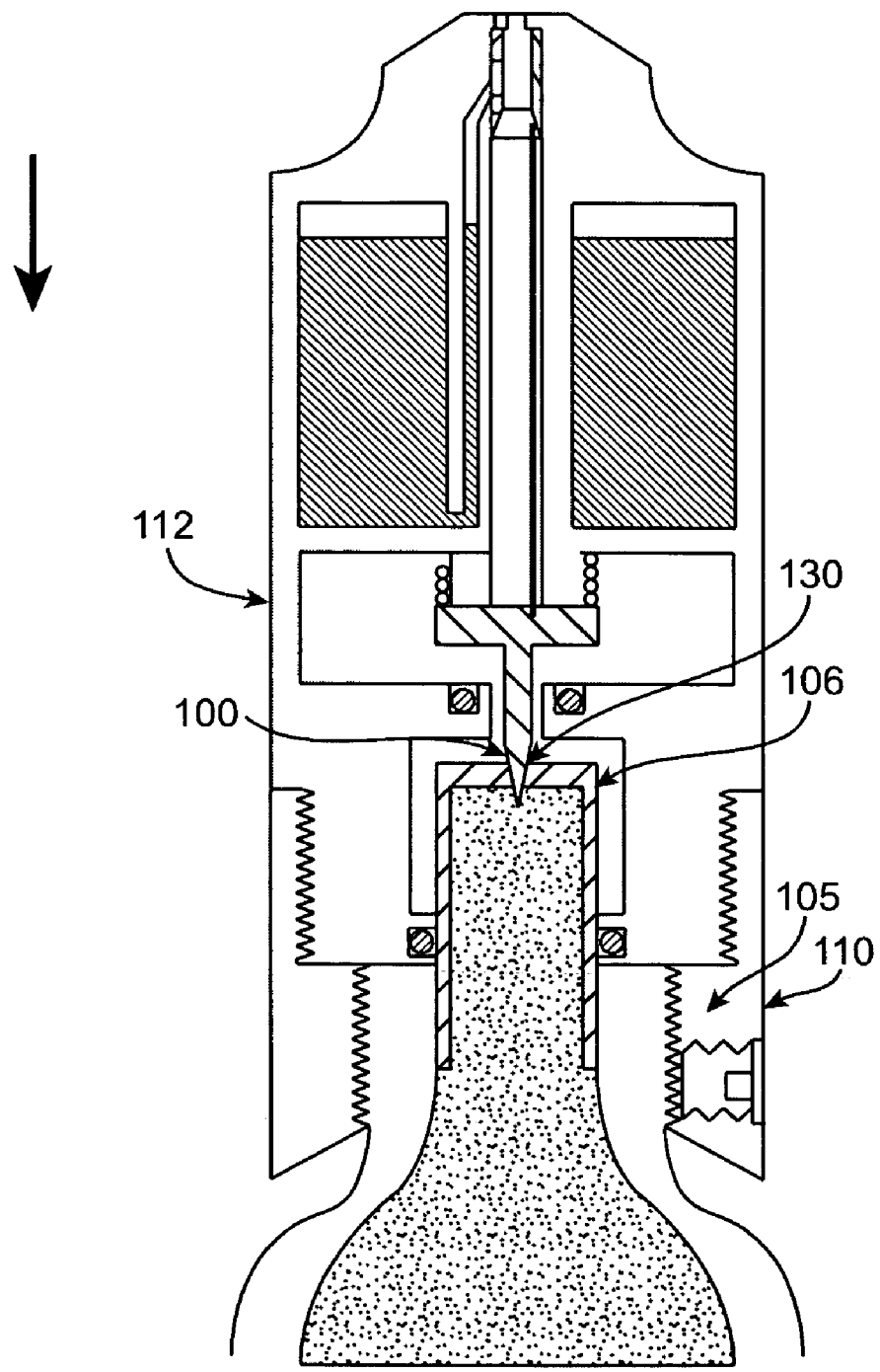
FIG. 2 shows the embodiment of FIG. 1 after activation.
Figure 3:
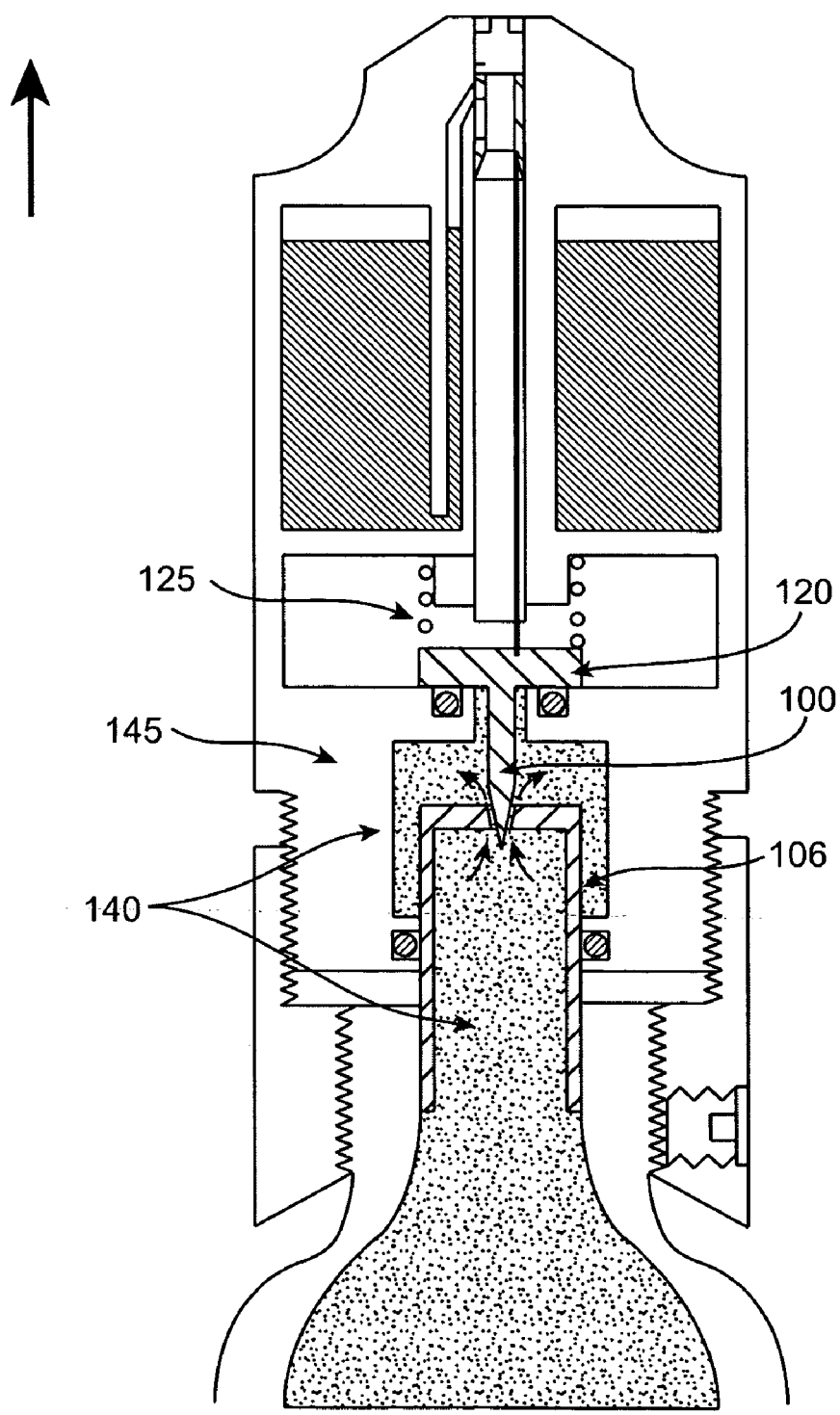
FIG. 3 shows the embodiment of FIG. 1 when charged with high pressure gas.

To activate the device initially, the rotatable head 112 is screwed downward the full distance possible into the fixed collar 110, causing the needle 100 it contains to penetrate the cap 106 that seals the cartridge 101 as shown in FIGS. 2 and 5*b*. Thereafter, when the rotatable head 112 is unscrewed slightly the poppet valve 120 on which the needle 100 is mounted is closed and the needle 100 is lifted out of the orifice 130 it formed in the cap. As shown in FIGS. 3 and 5*c*, this causes the chamber 145 between the cap 106 and the poppet valve 120 to become filled with high pressure $CO_2$ gas 140. The volume of the gas dose chamber 145 is important since it defines the quantity of $CO_2$ gas 140, i.e., the gas dose that is mixed and co-infused with the drug.

Figure 4:
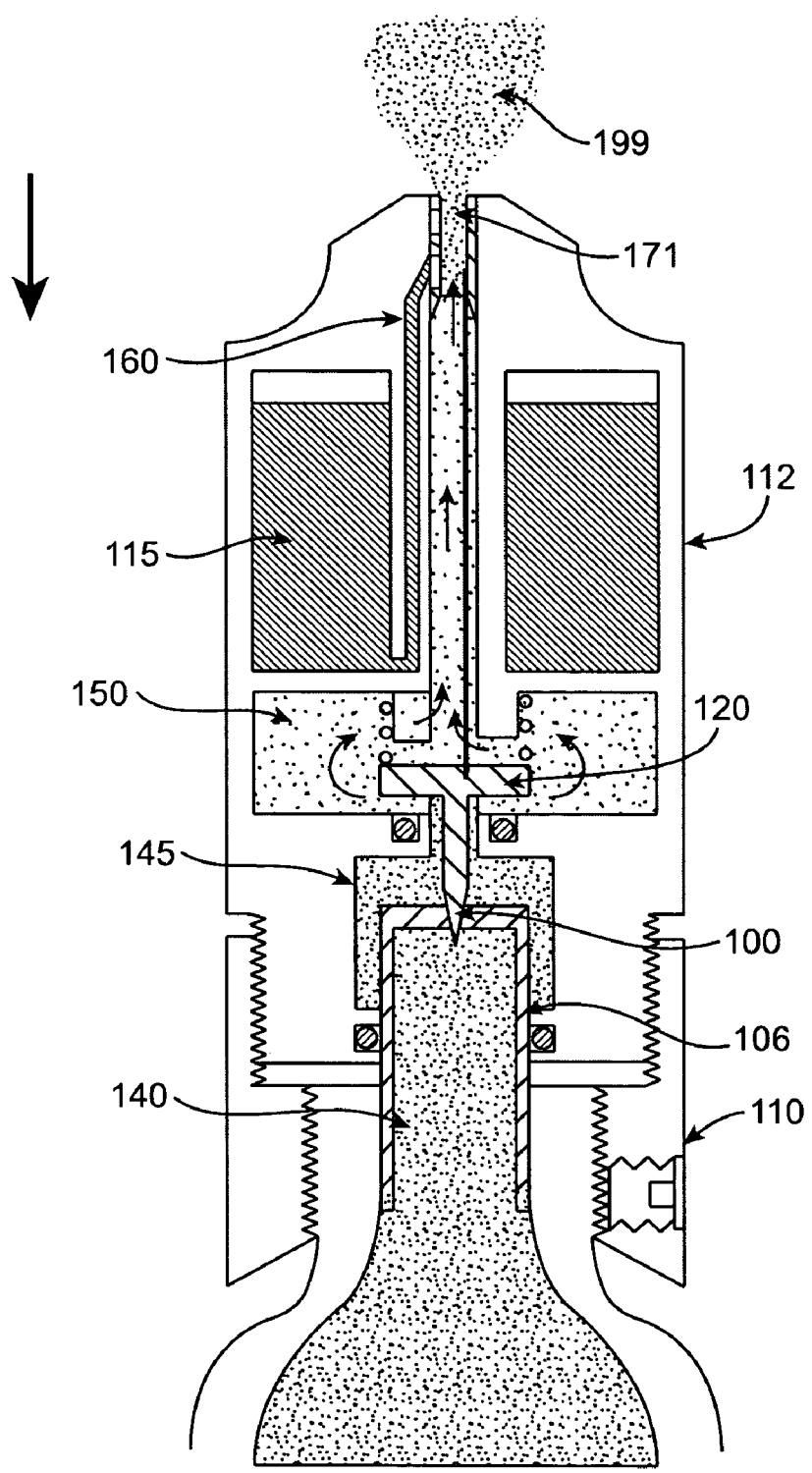
FIG. 4 shows the embodiment of FIG. 1 during discharge of the gas and drug solution.
Figure 6:
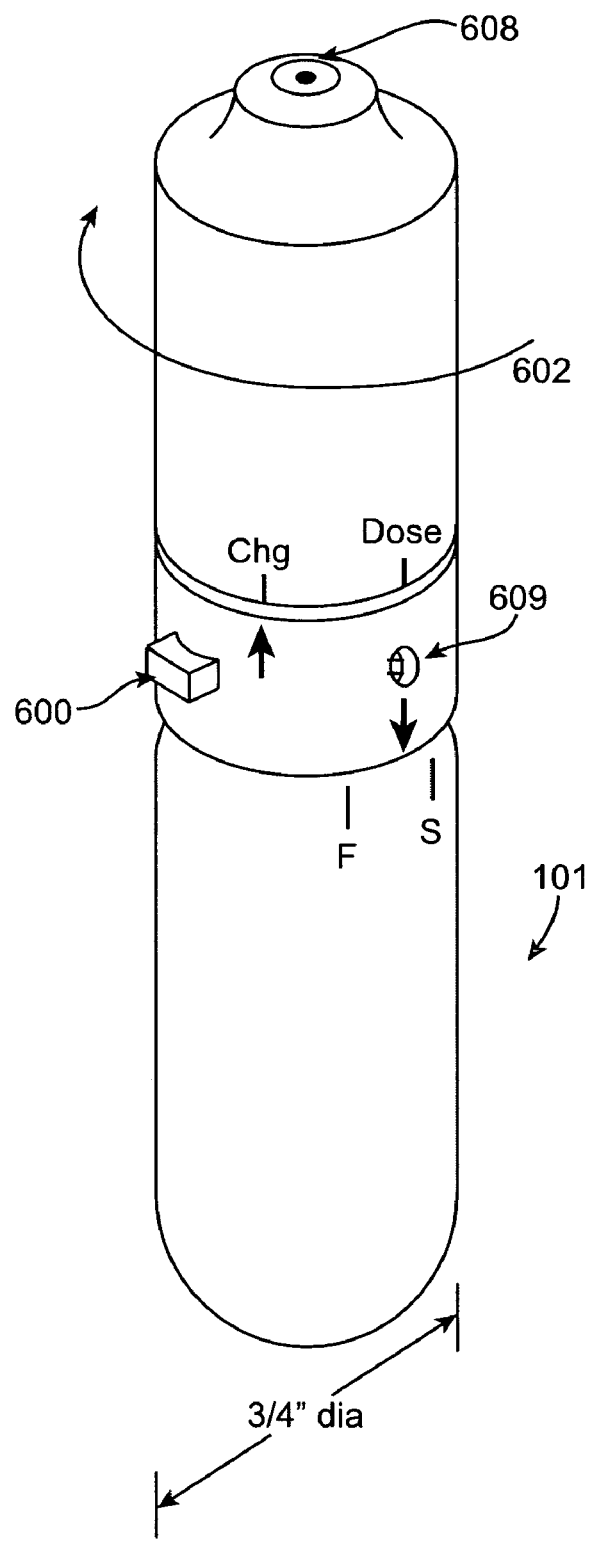
FIG. 6 shows the embodiment of FIG. 1 and illustrates the charge/dose and dose rate adjustment features of the embodiment.
Figure 7:
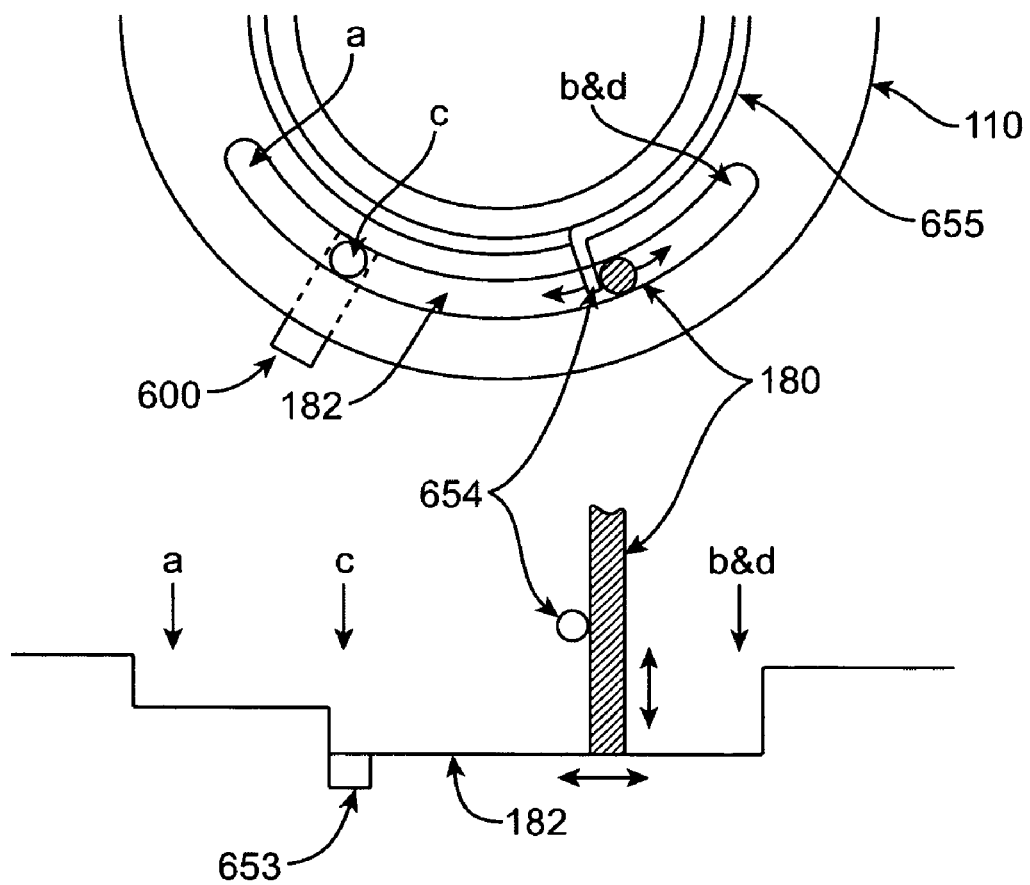
FIG. 7 shows the detail of position selection for controlling the dose rate.
Figure 7A:
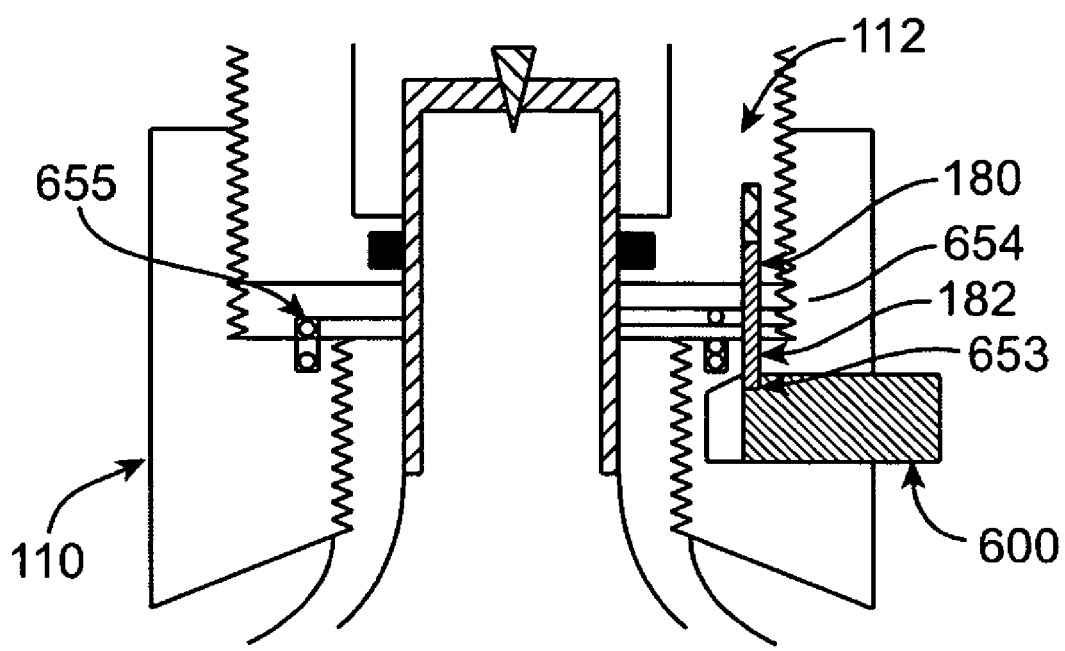
FIG. 7A shows another view of the embodiment and shows certain details of the charge/dose features.

The poppet valve 120 is biased shut against its O-ring-sealed seat 122 by a spring 125 that produces sufficient force to hold the poppet valve 120 shut against the force of the high pressure gas 140 on it. This force need not be large since the area of the orifice 130 sealed by the poppet valve 120 can be very small (a few $mm^2$). When the rotatable head 112 then is screwed downward the needle 100 seats in and seals the orifice 130 in the cap 106 and the poppet valve 120 is lifted as shown in FIGS. 4 and 5*d*, allowing the high pressure gas 140 in the gas dose chamber 145 to escape as a controlled burst into the gas plenum 150 which has a much larger volume, reducing the pressure ten-fold or more. After the dose is administered, the pressure in the gas dose chamber would be about 1 atmosphere. From the gas plenum 150 the gas passes through the exit passage 126 and the venturi constriction of the passage. The poppet valve 120 is attached to a venturi control wire 121 that operates sleeve 123. Sleeve 123 is constructed to include a hole or gap 124. The gap 124 is positioned in the sleeve 123 and the sleeve is positioned within the venturi region so that when the poppet valve 120 is closed the gap 124 is not aligned with the opening to the capillary passage 160. However, when the poppet valve 120 is opened as it is during the controlled burst, the venturi wire 121 lifts the sleeve 123 so that the gap 124 is aligned with the opening to the capillary passage 160. During the dose's passage through the venturi constriction, the controlled quantity of high velocity gas aspirates a correspondingly controlled amount of drug agent 115 through a capillary passage 160 from the drug reservoir 115. The $CO_2$/drug mixture 199 then is discharged as a dose of spray through a hole in the top 171 of the dispenser. Subsequent doses are ejected by repeating the charge and discharge sequence represented by FIGS. 3 and 4 or FIGS. 5*c* and 5*d* respectively.

The actions required by the user to execute this sequence are illustrated in FIGS. 6 and 7. To activate the device initially the user screws in the rotatable head 112 until it stops at the mark indicated as "Dose". The head is prevented from being unscrewed from its pre-activation position and is stopped at its fully screwed-in position by a sliding pin 180 in a slot 182 between the fixed collar 110 and the rotatable head 112. These limiting positions correspond respectively to the positions shown in FIGS. 1 and 2 (and to FIGS. 5*a* and 5*b*) and are labeled "a" and "b" respectively in the schematic drawing of the pin 180 and slot 182 shown in FIG. 7. To deliver doses, the user first rotates the head against a torque-producing spring 655, which includes a section 654 that is engaged with the pin 180, to the charging position "c" in FIG. 7 corresponding to FIGS. 3 and 5c, where the head 112 becomes locked by the pin 180, now held in a retaining well 653. The user then applies the top of the dispenser 608 to his nose or mouth and pushes a button 600 which releases the sliding pin 180 from its retaining well 653. The head 112 then rotates rapidly back to position "d" (corresponding to FIGS. 4 and 5d) under the action of the spring, completing the dose-delivering sequence of processes described in the preceding paragraph. As shown in FIG. 6, subsequent doses are delivered simply by "cocking" the device by rotation as shown by arrow 602 and pushing a button 600 to deliver the dose by an automatic counter-rotation. Note that left-handed screw threads are used in the embodiment shown, although a standard right-handed thread may also be employed. Accordingly, it is not necessary for the user to observe the position of the head relative to the collar 110 since the action involves rotation from the limiting position a in one direction to the limiting position d in the opposite direction. It will be clear to those of ordinary skill in the art that this same type of automatic action can be obtained also by combining a rotary cocking action with a triggered linear return between the charging and dose positions such as is found in the action of retractable ball-point pens.

For a device designed to dispense a particular drug, the volume of $CO_2$ gas in a dose, the quantity of drug that it aspirates and the rate of infusion of the mixture has to be chosen carefully. Obviously, the quantity of drug in a dose should be that determined in clinical trials and selected to be the most effective under a given set of circumstances, taking into account the enhanced effect of the drug caused by the co-application of $CO_2$. However, the quantity of $CO_2$ accompanying each drug dose may not necessarily be that determined in clinical trials to obtain the optimum potentiation, since both the quantity and concentration of $CO_2$ infused and the rate of its infusion must be acceptable to the user.

The relative quantities of drug and $CO_2$ in the dispensed mixture are determined by the relative diameters of the capillary opening 161 and the venturi throat 155. The rate of discharge of the mixture is limited by the series flow impedance from the dose chamber 145 through the poppet valve 120, plenum 150, and venturi 155. Generally, the tolerable steady flow rate of gaseous $CO_2$ into the nose is in the range 2–10 cc/sec for at least 2 seconds corresponding to the approximate volume of the nasal and sinus passages. However, patients may develop a short-term tolerance after continuous use or successive uses that allows for a higher flow rate. In addition, the inventors have access to new experimental evidence that suggests that under certain circumstances much higher initial flow rates, on the order of 1 to 2 liters/minute may not only be tolerated, but be beneficial, in relief of certain symptoms. The tolerable $CO_2$ infusion rate is more than 10 cc/sec for an indefinitely long period into the mouth. However, although other designs may be appropriate in specific circumstances, in a dispenser for general adult use that includes nasal infusion, the gas dose chamber 145 at minimum can contain an amount of gas corresponding to 4–20 cc at room temperature and atmospheric pressure. If the $CO_2$ pressure in the cartridge 101 and in the dose chamber 145 is nominally about 60 atmospheres (which is achievable by known cartridge designs—although such cartridges are not necessarily currently marketed for medical use), the volume of the dose chamber 145 should be in the range 0.07–0.33 cc, equivalent to a cubic chamber with 4–7 mm edge length. The diameter and height of the gas dose chamber 145 therefore need to be only slightly larger than the typical 3½ mm sealing cup diameter of currently available cartridges. A different size gas dose chamber would, of course, be required given different pressure, desired volume of gas, or other changes in the assumptions described. The concentration of the drug solution and the relative sizes of the venturi 155 and capillary openings 161 are chosen for the expulsion of this quantity of $CO_2$ to aspirate the clinically appropriate drug dose (typically 10–60 mg for many drugs), although trials may show that some individuals prefer more than one application of $CO_2$ to obtain a full drug dose.

Because the desirable flow rate of gaseous $CO_2$ has been found to be highly user-subjective, it is preferable to have a means for the user to select the dose speed, i.e., the period over which the gas and drug dose is delivered as a pulse. After the device is activated as is shown in FIGS. 2 and 5b, the dose speed can be modified conveniently and simply in the illustrative embodiment by loosening the set-screw 111 that prevents collar rotation, unscrewing the collar 110 to the desired, marked positions 609 as shown in FIG. 6, and re-tightening the set-screw 111. The fastest dose delivery is obtained in the post-activation position (FIGS. 2 and 5b) since the poppet valve 120 is opened fully in that position, but if the collar 110 is unscrewed, the poppet valve 120 is adjusted so that it is only very slightly open when the head is at position "d". That position would correspond to the minimum flow rate required for aspiration of the proper quantity of drug. The range of adjustment between the positions of the collar 110 giving maximum and minimum permissible flow rates, shown as "F" and "S" in FIG. 6, is limited by the width of the slot 182 in the threaded cartridge neck 105 in which the set-screw 111 is seated.

It is anticipated that additional features may need to be included to make the various chambers and passages easily manufacturable, and other aspects not shown could be incorporated in the design of a commercial product.

Dispenser Means for Co-Application of $CO_2$ and Drugs by Inhalation and Infusion The embodiment of the invention described above is a means for co-infusion or co-inhalation of a $CO_2$/drug mixture as a measured dose into the nasal and respiratory passages. That device and the devices described in U.S. application Ser. No. 09/614,389 are not generally suitable for inhalation of $CO_2$ into the lungs to potentiate the effect of drugs applied by other means. During inhalation the $CO_2$ is mixed with inspired air; therefore, a flow rate and quantity of $CO_2$ much greater than that achievable with the dispenser embodiments previously described is necessary. The required flow rate for co-application of drugs and of $CO_2$ by inhalation, and the means for achieving the required flow rate in a portable device are now described.

In particular embodiments, the therapeutic gas may comprise essentially pure carbon dioxide. By "essentially pure," it is meant that the carbon dioxide, or other therapeutic gas, is free from the significant presence of other gases, i.e., the total volume of gas will comprise at least 50% carbon dioxide, preferably at least 70% carbon dioxide, and more preferably 95% or greater. In addition to being free from other gases, the carbon dioxide will be free from other physiologically or biologically active components, such as drugs, surfactants, and other substances that, although present at relatively low concentrations, would have physiologic or biologic effect.

In general, depending on the size and other attributes of the individual, 1 to 2 liters of air inspired over a period of 1 to 2 seconds is comfortable for most adults. This corresponds to a flow rate range of 1 to 4 liters/second of air. The concentration of $CO_2$ in expired breath is about 6%. Most experimental research with inhalation of $CO_2$ by humans and animals has employed maximum concentrations of approximately 10%–70% $CO_2$ in air. However, above 10% concentration the individual may suffer a feeling of suffocation, and above 30% continued inhalation will result in the individual losing consciousness. If a 10% concentration of $CO_2$ is desired, a dispenser that provides a controlled flow rate in the range 100–400 cc/sec is needed. This is more than an order of magnitude greater than the typical maximum tolerable initial flow rate for infusion of 100% $CO_2$ into the respiratory passages for which the previously described embodiments are suitable.

Figure 8:
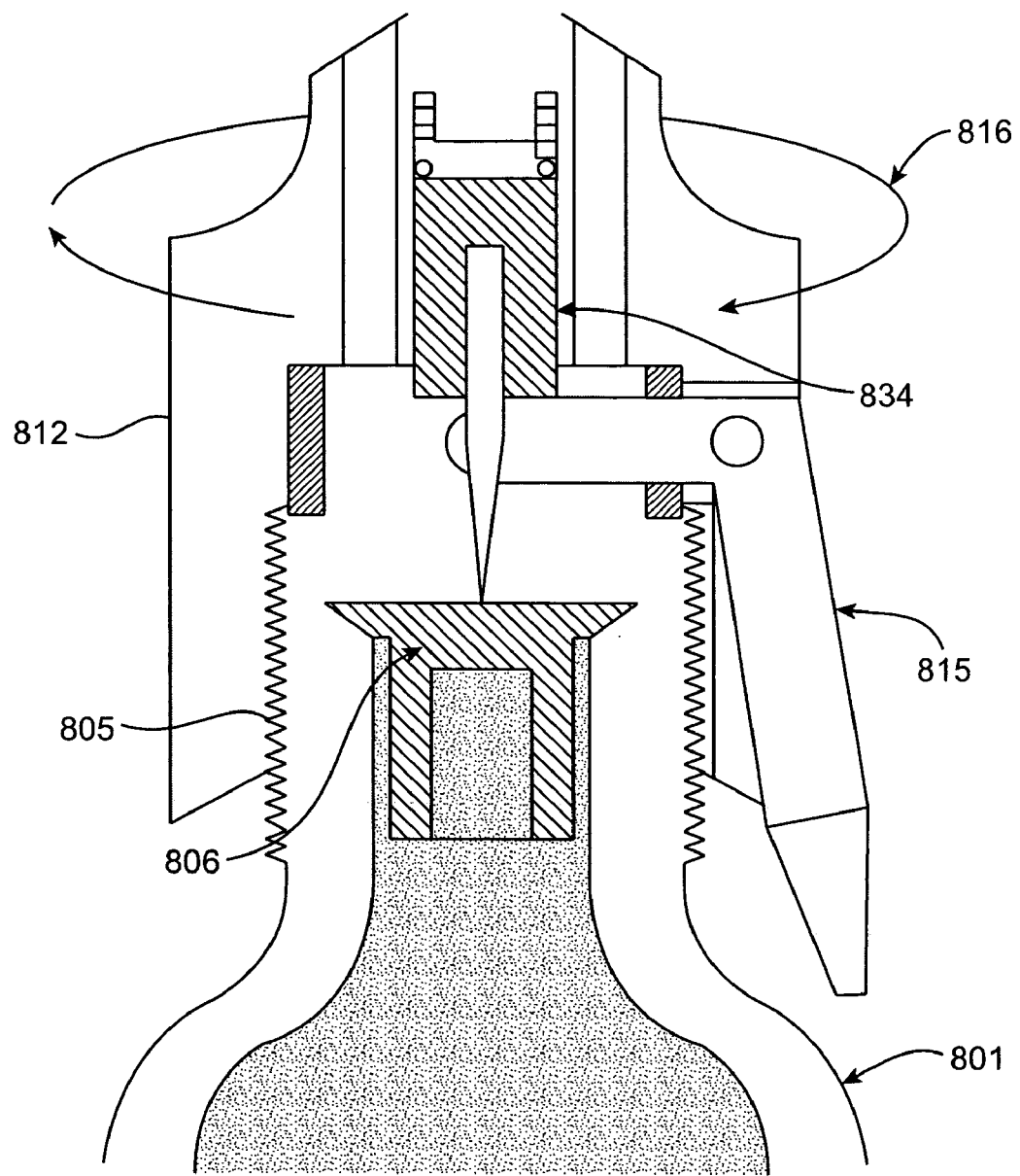
FIG. 8 shows a second embodiment of a device which may be particularly appropriate for inhalation of the gas.
Figure 8A:
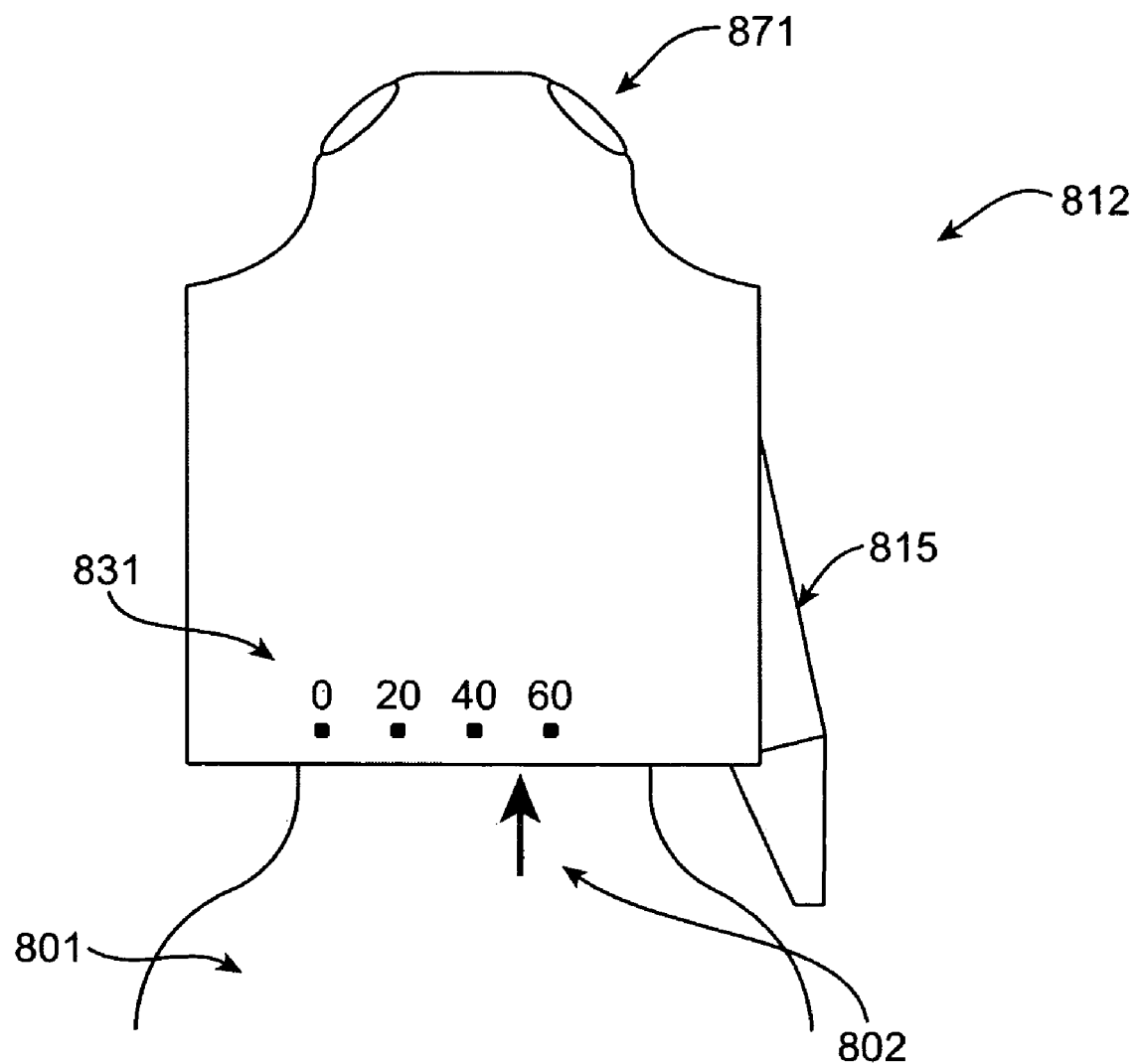
FIG. 8A shows the detail of the flow rate adjustment and selection for the second embodiment.

FIGS. 8–11 show a dispenser embodiment for controllably delivering $CO_2$ at an adjustable rate in the 100–400 cc/sec range suitable for co-application of $CO_2$ with drugs by inhalation or for treatment of asthma and other conditions by inhalation of $CO_2$ alone. The dispenser embodiment in FIGS. 8–11 is similar to that described for $CO_2$ infusion in U.S. application Ser. No. 09/614,389 in that it is a hand-held portable dispenser consisting of a pressurized cylinder of $CO_2$ screwed into a dispenser head assembly. The $CO_2$ cartridge 801 in this embodiment has a threaded neck 805 and a plug-type sealing cap 806 and is screwed into a dispenser head with a seal-perforating needle 800 similar to that described in U.S. application Ser. No. 09/614,389. In the device as marketed to the user, the cartridge 801 is screwed into the head 812 until the tip of the needle 800 just touches the top of the intact sealing cap 806 (i.e. without penetrating it) as shown in FIG. 8. The user activates the device by screwing the cartridge 801 onto the needle-bearing head 812 as indicated by arrow 816, thus perforating the sealing cap 806. The user may select the rate at which the device can deliver $CO_2$ gas by choosing the distance that the needle 800 penetrates the cap 806, and thereby the size of the orifice 830 produced in the cap. The device would be activated by unscrewing the head and depressing the lever to release the gas. The degree of rotation required to produce each selectable rate may be indicated by number or other indicator markings on the dispenser head as shown in FIG. 8a.

Figure 9:
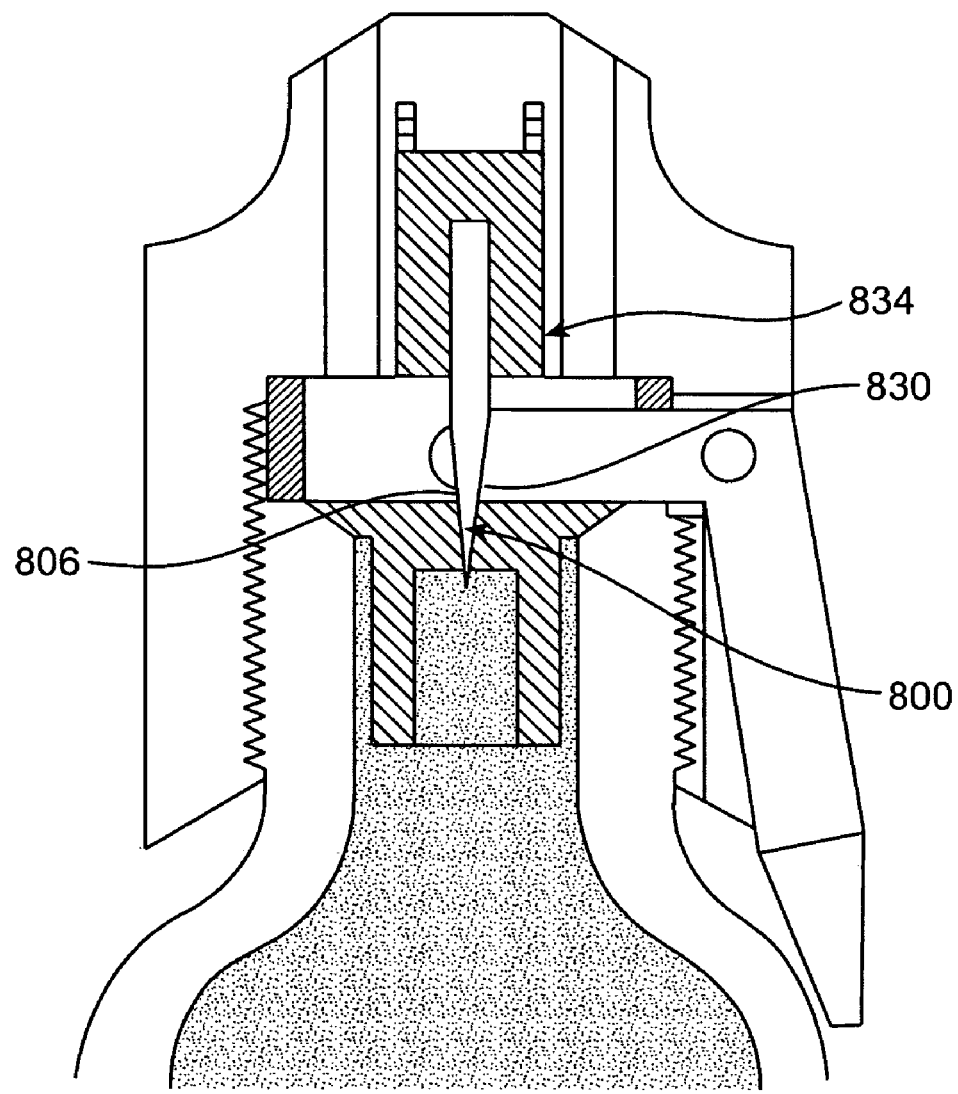
FIG. 9 shows the embodiment of FIG. 8 after perforation of the cap in a locked position.

However, while it is possible to select the flow rate by screwing the cartridge 801 only part way onto the head 812 to achieve the degree of seal perforation by the needle 800 required to obtain that rate, it is preferable to screw the cartridge 801 and head 812 together as far as possible, making the maximum possible orifice in the sealing cap 806. In this position, which is shown in FIG. 9, gas cannot be released from the cartridge 801 since the needle 800 is locked in its fully seated position. The user can select this position, therefore, to carry the device without risk of unintentional release of $CO_2$ gas. Since both the pressure in the cartridge and the orifice size are known, the maximum flow rate is also known. As shown in FIG. 8A, in this preferred embodiment, the device is activated for use by partially unscrewing the head 812 as is indicated by arrow 817, shown in FIG. 10, until the arrow 802 on the cartridge 801 is opposite the marking 831 on the head 812 that indicates the flow rate that the user desires. This flow rate is essentially a portion of the known maximum flow rate permitted by the size of the orifice, and the markings may be an arrow 802 on the cartridge and numbers 831 on the head that represent either a percentage of the maximum flow or the number of cc/sec.

Figure 10:
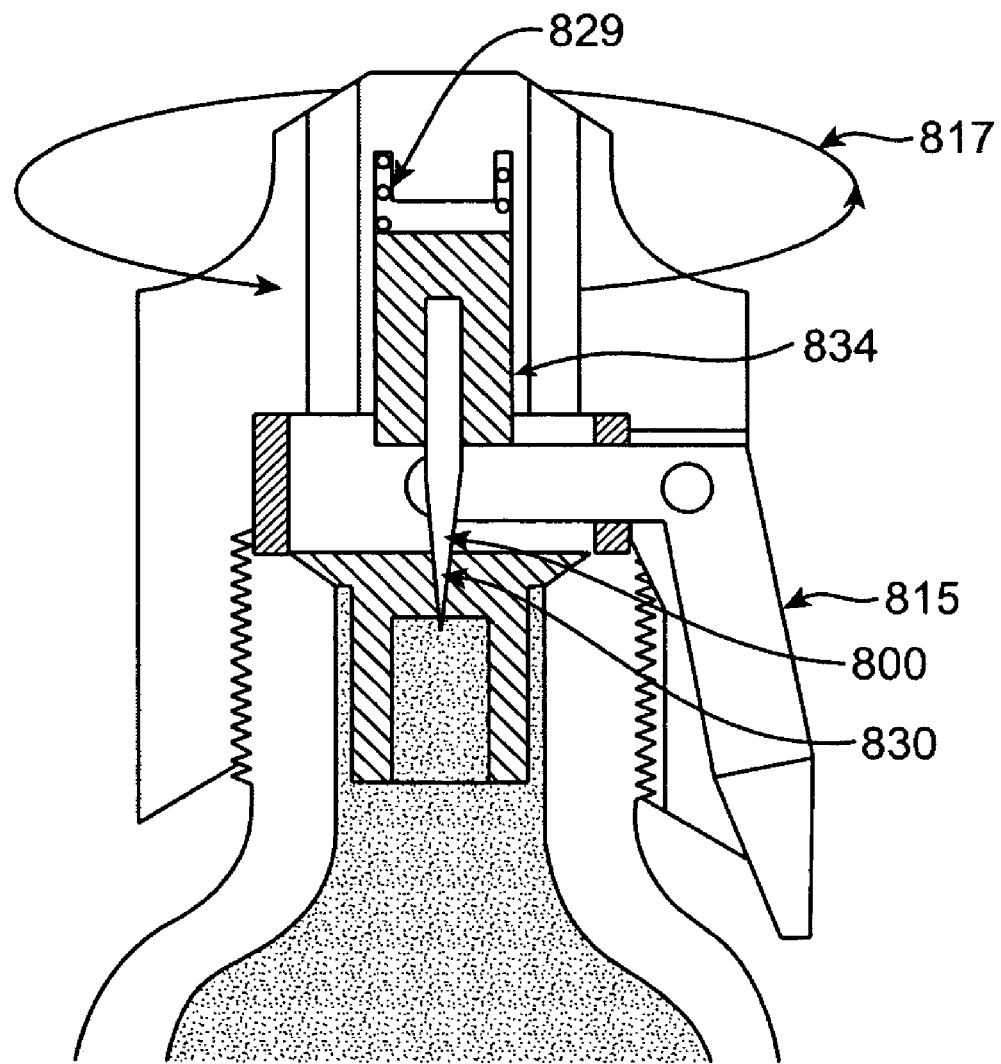
FIG. 10 shows the embodiment of FIG. 8 in the activated position.
Figure 11:
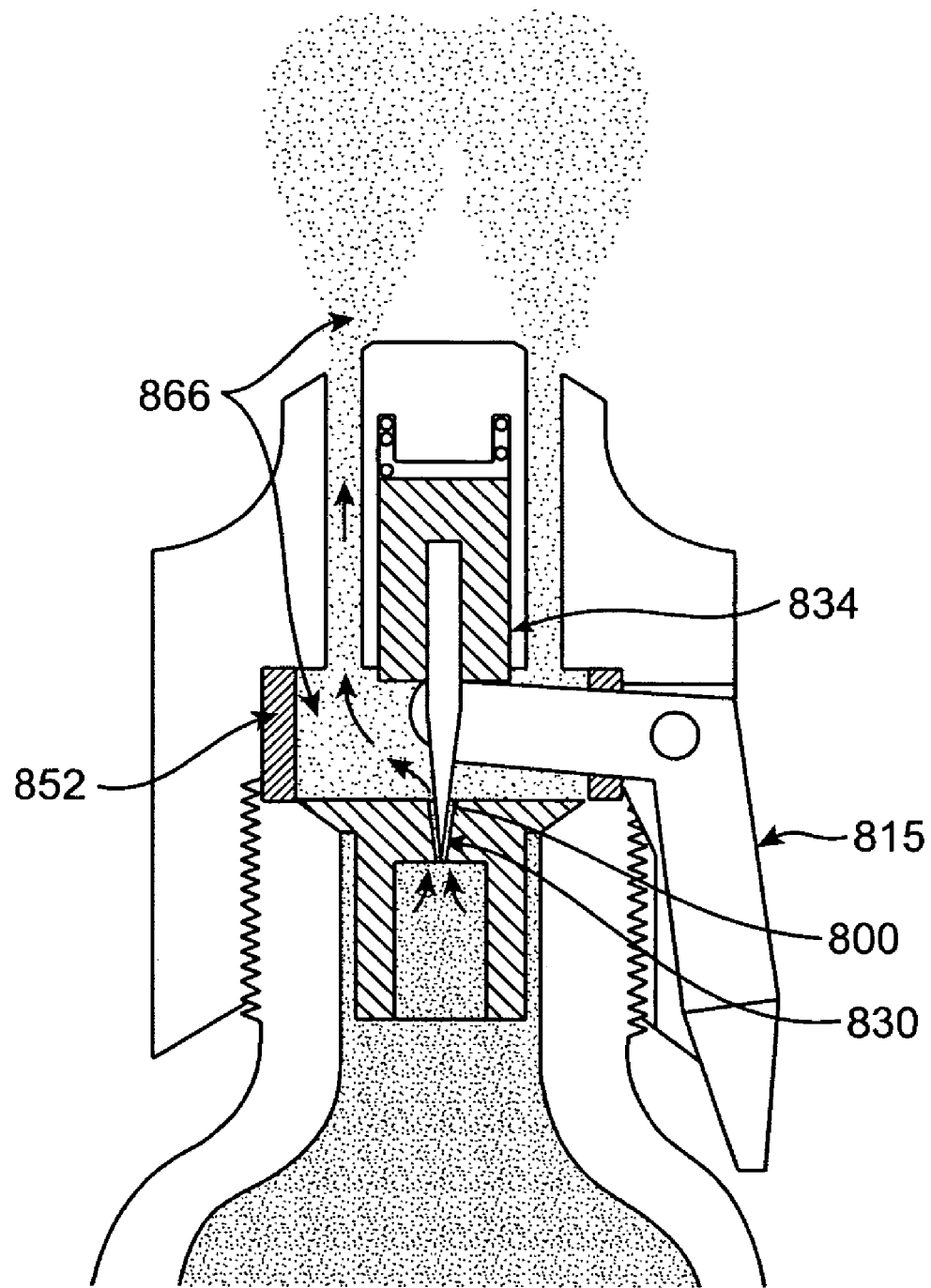
FIG. 11 shows the embodiment of FIG. 8 when dispensing gas.

Upon activation, the head 812 and cartridge 801 are in the position shown in FIG. 10. In the present embodiment the needle 800 is held firmly seated in the cap orifice 830 by the force of a spring 829 acting on a sliding needle mount 834 as shown in FIG. 10, thus preventing flow of gas from the cartridge 801. In the present embodiment gas 866 can be controllably released up to the desired flow rate by depressing the dispensing lever 815 as shown in FIG. 11. The lever 815 lifts the sliding needle mount 834 and thereby unseats the needle 800 to open, directly and variably without rotating the head 812, the orifice 830 in the cartridge 801 seal to obtain the desired high flow rate. A compressible (sponge-type) gasket ring 852 seals the dispenser lever penetration and threads to prevent excessive gas leakage from the low pressure gas region. When the lever 815 is released, the spring 829 returns the needle mount 834 and needle 800 to the fully seated position as in FIG. 10, terminating the gas flow 866 from the openings in the top of the head 871. To repeat the flow, the user again presses and releases the dispensing lever 815. After the dispensing process is completed, the user can screw the head back to the locked position shown in FIG. 9 for secure transport in a pocket or purse.

The direct lever-actuated motion of the needle sliding mount 834 permits the greater linear motion of the needle 800 out of the orifice 830 that is required to obtain a high flow rate. Therefore, provided that the orifice 830 is large enough, using this device, the user can selectively obtain the higher flow rates needed for inhalation of $CO_2$. The controllability and simplicity of the needle-in-cap flow rate selection and adjustment, employed in previously described embodiments, is retained without the requirement of a large or coarse rotation of the head to a high flow position.

Figure 12A:
FIGS. 12A–E show application of gas to the nose, mouth, both nostrils, eye and ear using an embodiment of a gas dispenser.
Figure 12B:
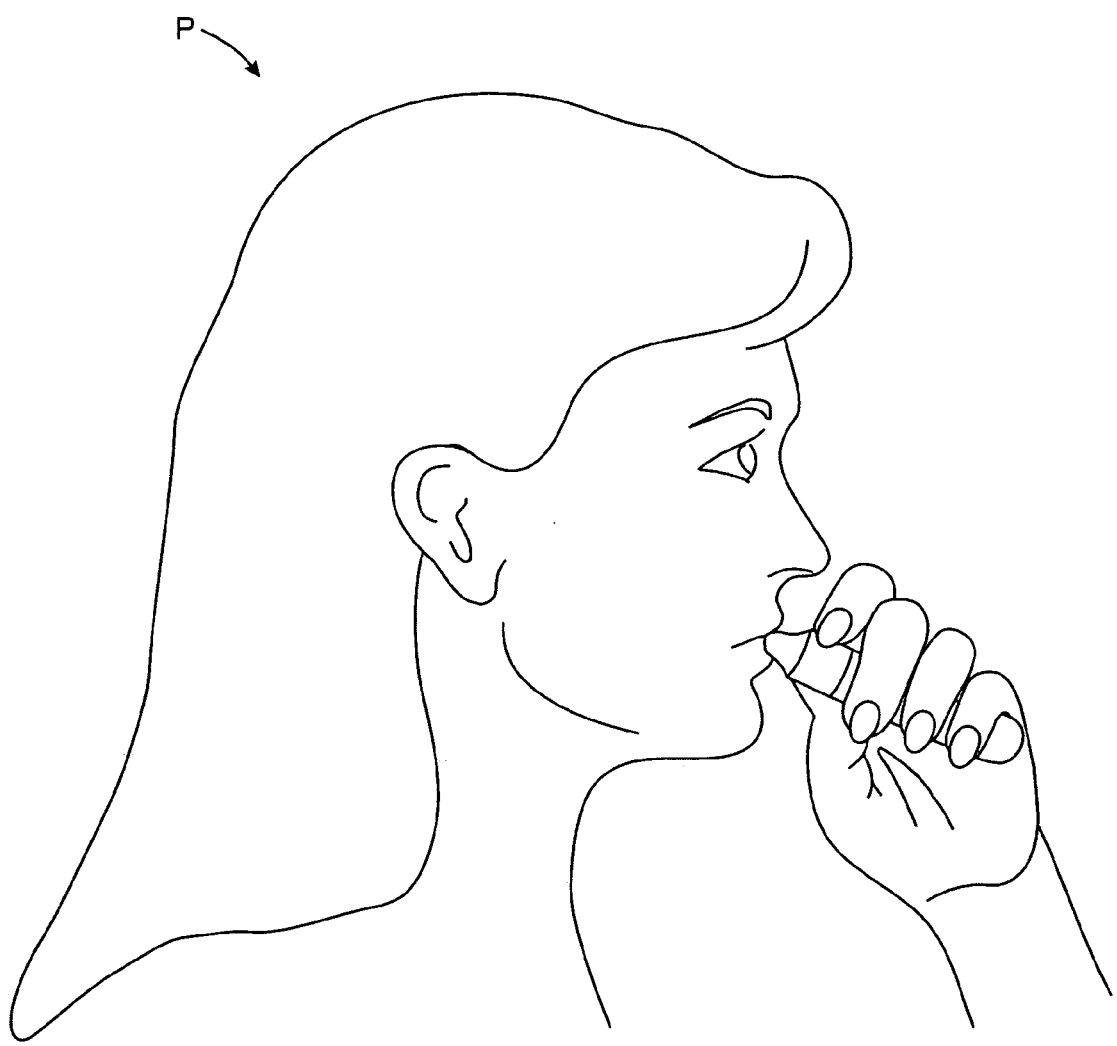
Figure 12C:
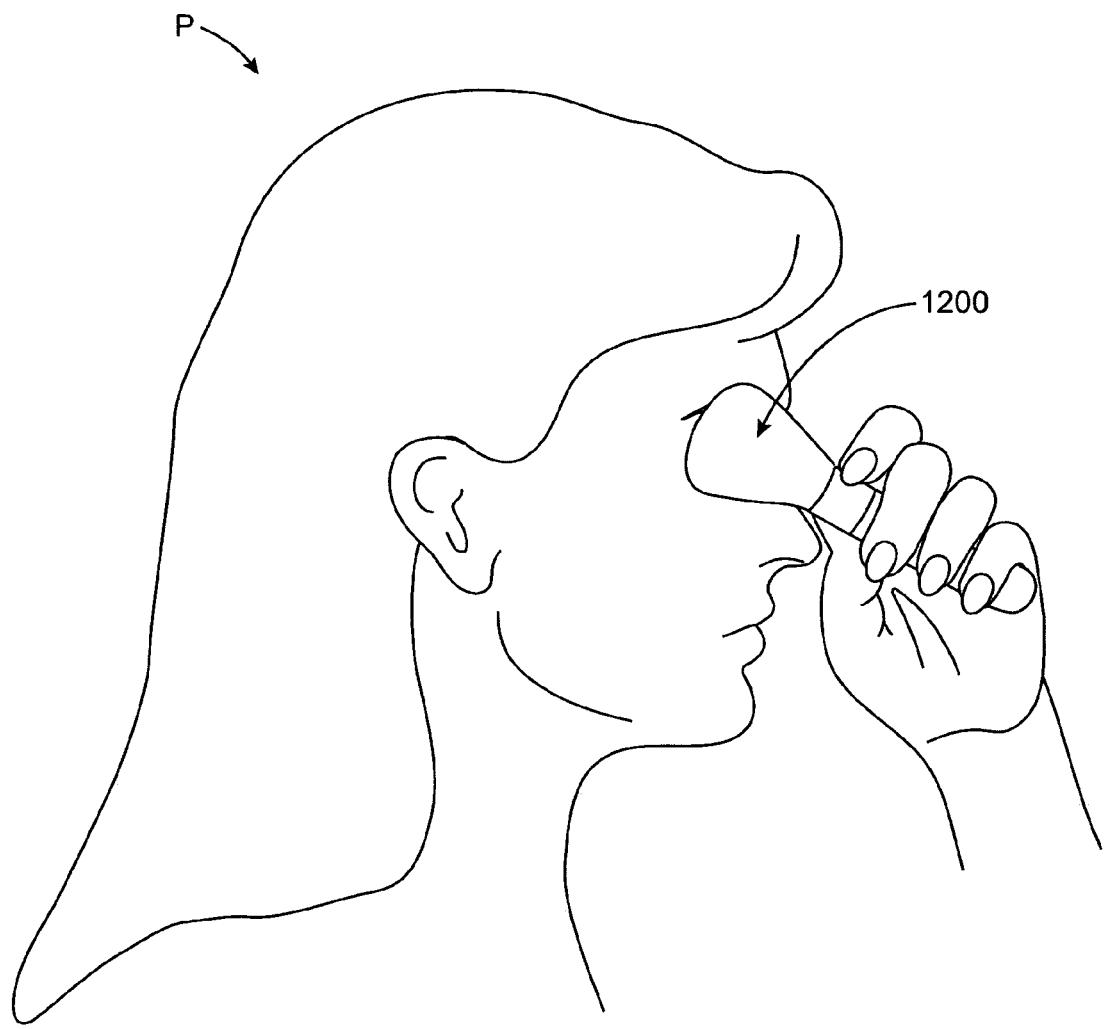
Figure 12D:
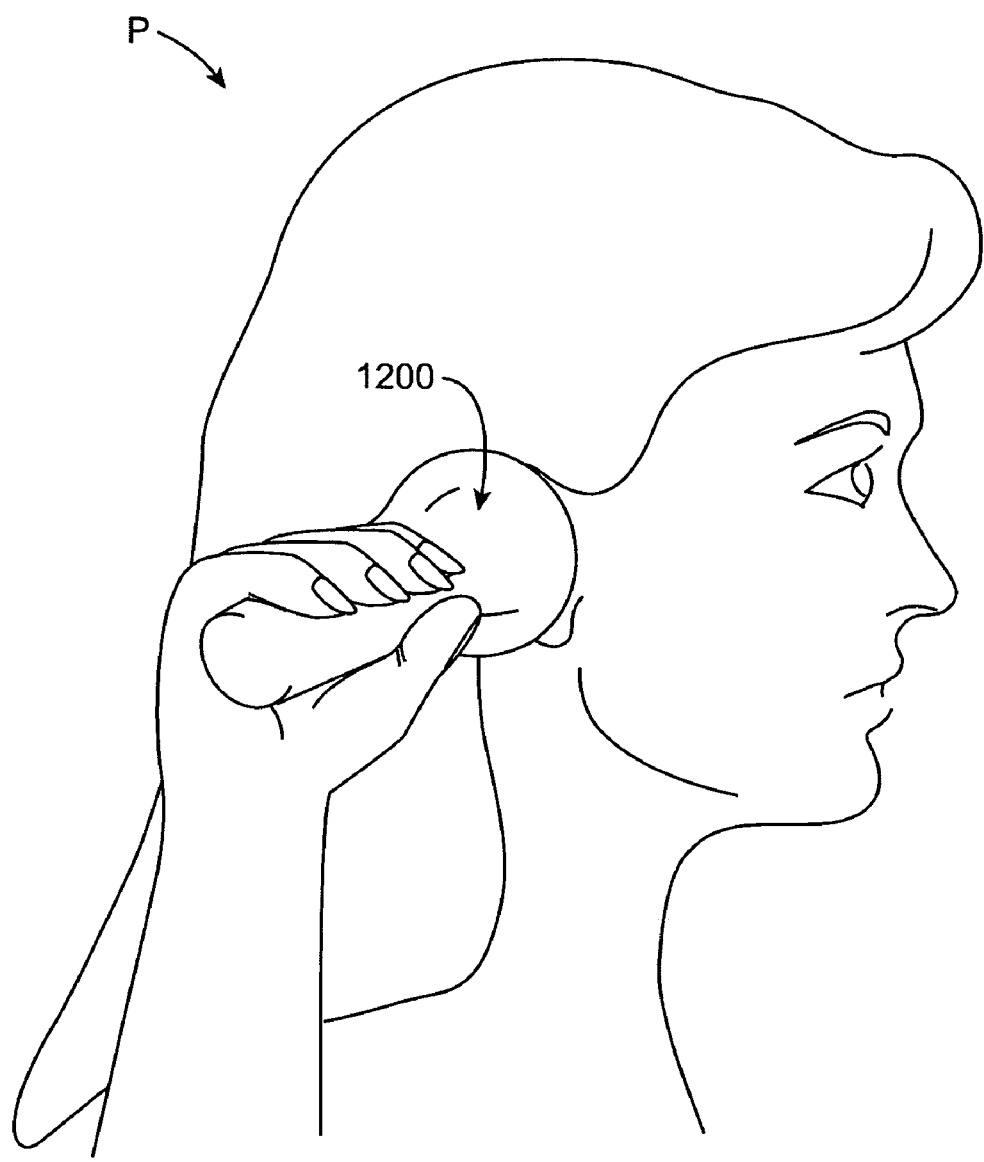
Figure 12E:
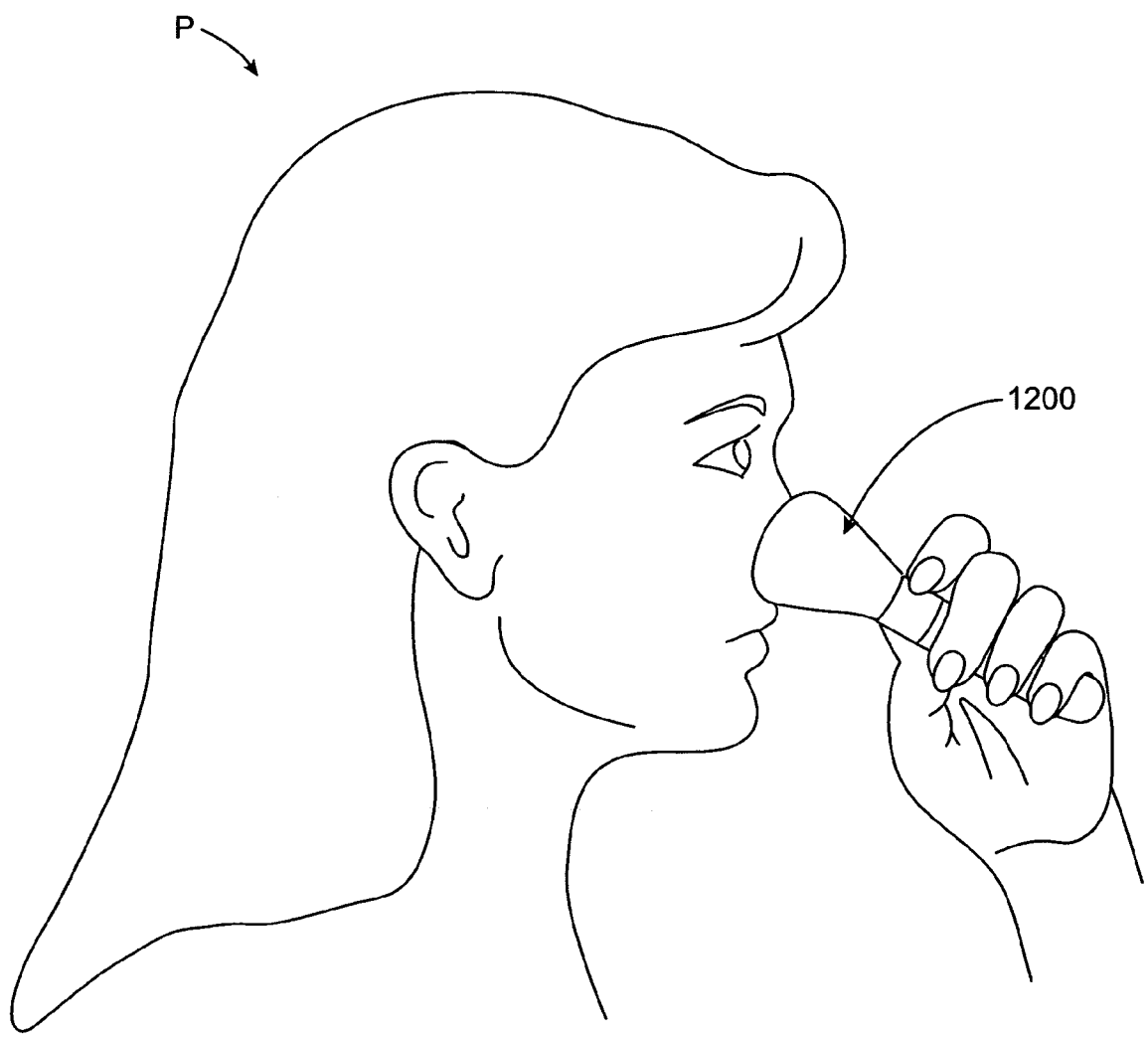

It is also possible to potentiate drug action solely by mucosal infusion. While generally, infusion is best performed using an initial lower flow rate, on the order of 0.5 cc/second to 20 cc/second depending on the tolerance of the particular individual, certain applications allow and may even require a high initial flow rate. The lever activated embodiment may be modified to provide a low flow rate, but the rotably activated embodiments described in U.S. application Ser. No. 09/614,389 are also suitable, and indeed any low flow source of gas could be used. The general method of application is as follows: the selected drug is applied by any standard method including but not limited to inhalation, pills, capsules, injection, or epidural patch. As shown in FIGS. 12A–B, the individual P then infuses oral and nasal mucous membranes by placing the source of low flow rate $CO_2$ or other appropriately physiologically active gas or vapor in or around a facial orifice, such as the mouth or nostril, while substantially inhibiting the flow of the $CO_2$ into the trachea and lungs by limiting inhalation of the $CO_2$. If the mouth is infused the gas is allowed to exit from the nostrils. Alternatively, one or both nostrils may be infused either by using the dispenser head shown in FIG. 12B or by use of a cup or similar device that covers both nostrils as shown in FIG. 12E. The gas is allowed to flow from a remaining open orifice, i.e., either the mouth, the uninfused nostril, or both as appropriate. Completely holding the breath is not necessary to substantially prevent inhalation of the $CO_2$. With practice, it is possible for the individual to breathe through an uninfused orifice: for example, if one nostril is infused and the gas is allowed to exit though the other nostril, it is possible for the individual to breathe through the mouth without substantial inhalation of the infused gas. The eye or eyes may also be infused using a cup as shown in FIG. 12C or merely by holding a hand over the eye and releasing the gas between the hand and the eye. Persons of ordinary skill in the art will appreciate that a double cup could be developed to infuse both eyes simultaneously, and similarly appropriate heads could be developed to infuse the mouth and one nostril. The ear or ears may also be infused as shown in FIG. 12D. Note that a similar process may be used with the first embodiment to infuse a mixture of a drug and gas into various facial orifices.

Infusion can be continued to the limit of tolerance or until the desired potentiation effect is realized. Since most individuals develop a temporary increased tolerance after extended applications or repeated applications, it may be possible and desirable to increase the duration of additional infusions after a few applications when all applications occur within a short time of each other, i.e., approximately 1 to 20 minutes between each application.

Optional Features

Depending upon the particular market for and/or intended use of the particular dispenser, some or all of the additional features may be added to the embodiments described above, and may also be incorporated into the embodiments described in U.S. application Ser. No. 09/614,389.

Dilution of $CO_2$ with Air

Figure 13:
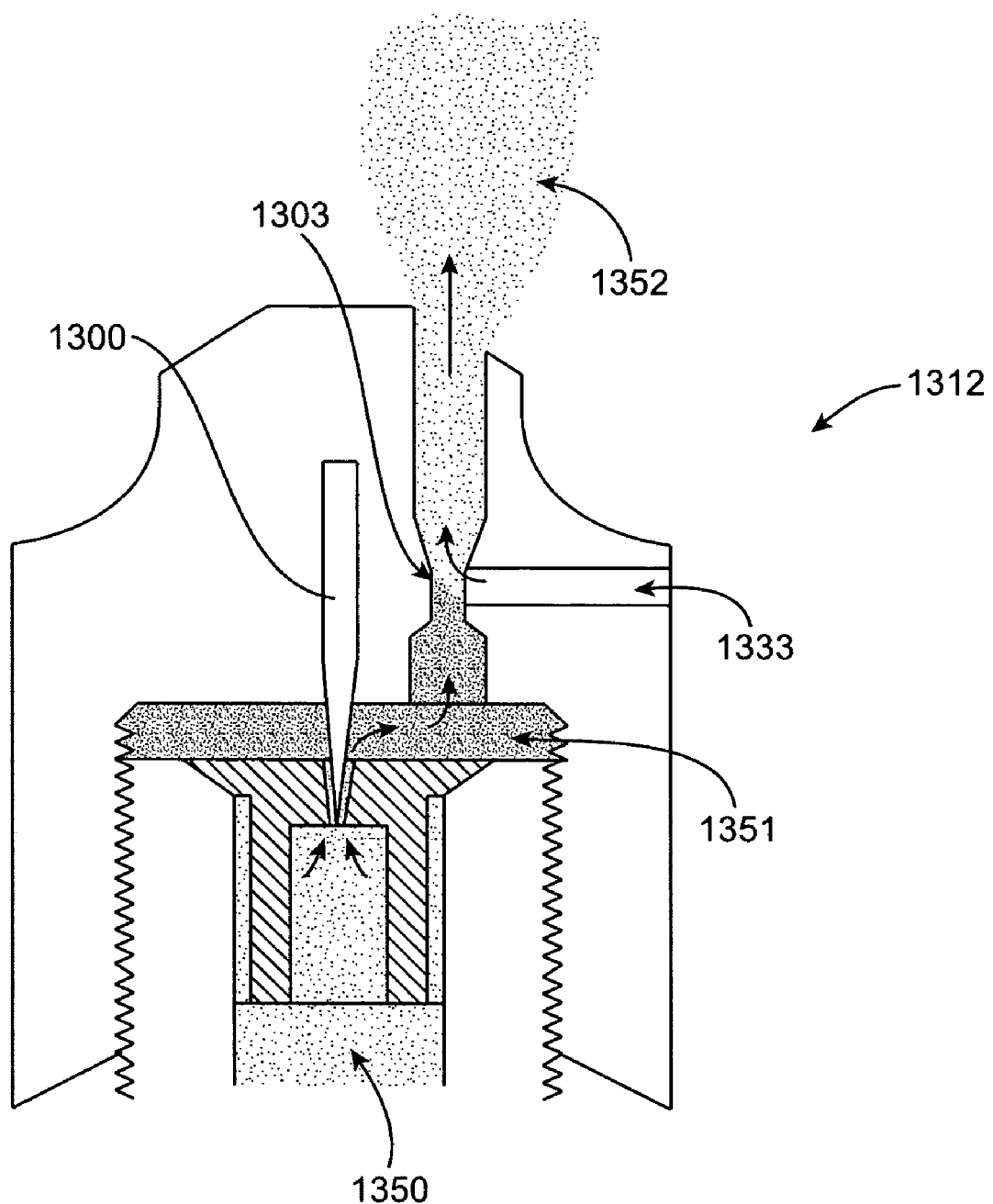
FIG. 13 shows an optional feature for dispensers which allows for dilution of the gas with ambient air.

As shown in FIG. 13, a venturi 1303 region can be added to the dispenser head 1312 that allows a quantity of ambient air to be mixed with the $CO_2$ dispensed. The high pressure $CO_2$ 1350 flows past the needle 1300 and becomes low pressure $CO_2$ 1351. The low pressure $CO_2$ moves past the air inlet 1333 and mixes with ambient air. The concentration of $CO_2$ in the dispensed gas 1352 will thus be lower than 100% to the degree that air is admitted into the air inlet 1333. This will, in part, be a function of the size of the air inlet 1333. Additionally, the user can place his finger wholly or partially over the inlet 1333 to adjust the $CO_2$ concentration to that which is optimum for him at a given time, e.g., at a given stage of nasal inflammation or other mechanical partial blocking means may be used with the same effect. This dilution feature also extends the duration of application obtainable from the dispenser for a fixed quantity of $CO_2$.

Differential Flow Adjustment

Figure 14:
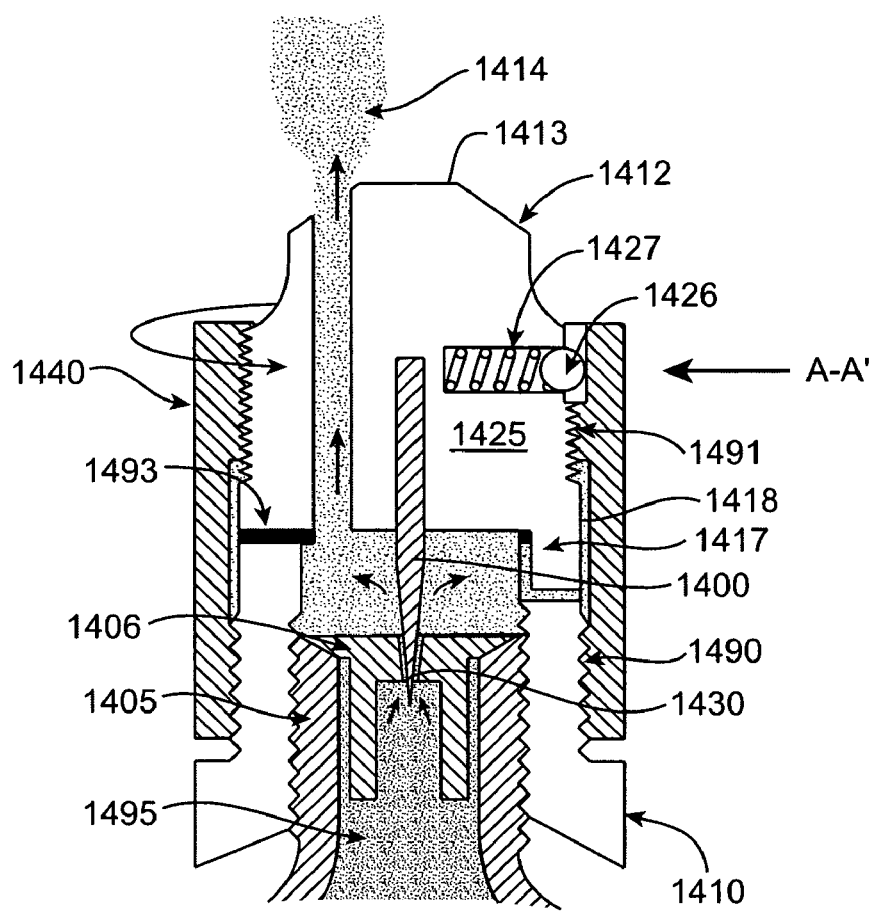
FIG. 14 shows an optional differential flow adjustment feature including the use of a ball detent particularly useful for low flow dispensers.

With reference to FIG. 14, in the initial embodiments described in U.S. application Ser. No. 09/614,389, the flow of $CO_2$ is adjusted by screwing the cartridge neck into and out of the dispenser head, thereby moving the needle into and out of the orifice in the cartridge seal. Although this is an extremely simple and practicable means for flow adjustment, it requires an extremely fine thread on the cartridge neck especially for the conventional needle size and shape described in FIG. 4A of U.S. application Ser. No. 09/614,389. This can be understood by considering that the axial movement of the needle required to obtain the required 2–10 cc typical flow rate is in the vicinity of 1–2 thousandths of an inch (mils). For the standard threaded cartridge using 24 threads per inch, this means that the full range of flow rate adjustment is obtained with rotation of the head less than $1/20^{th}$ of a turn (less than 20°). As described in U.S. application Ser. No. 09/614,389, the required rotation for convenient control of the typical maximum flow rate is in the range of 30° to 120°, with the optimum being near but less than 120° rotation. This means that a very fine thread on the cartridge neck 1405, more than 100 threads per inch, is required to approach the optimum degree of flow rate control by the means described in U.S. application Ser. No. 09/614,389.

While the production of such very fine threads is possible in principle, their production in a mass-produced low-cost device may be impractical for several reasons. First, machining such fine high-precision threads is substantially more expensive than machining standard threads on cartridge necks, and such threads would be expensive to produce on a molded plastic head. Second, cartridge threads now are generally protected from corrosion by applying a coating that would fill and clog fine threads. Third, it is impractical to hand-assemble items with such very fine threads because highly precise alignment is required to avoid cross-threading, resulting in a need for an expensive high-precision assembly machine.

Figure 14A:
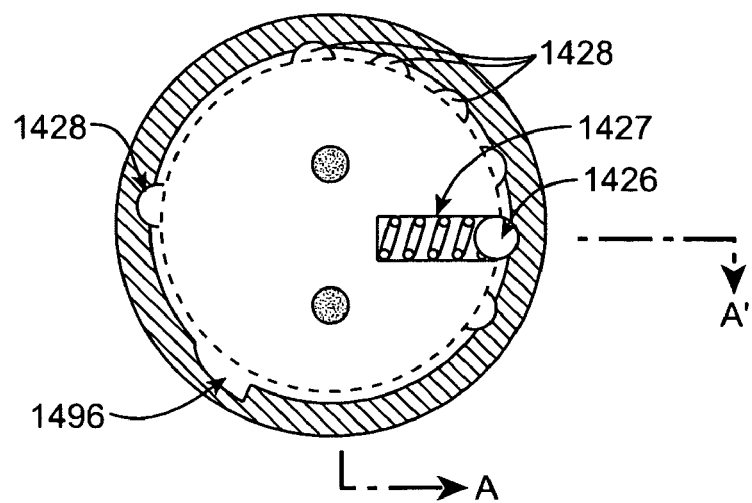
FIG. 14A shows a cross-section detail of the embodiment of FIG. 14A.

FIGS. 14 and 14A illustrate an embodiment of a low flow dispenser incorporating a differential screw threads that allow the user to obtain the required degree of rotational control with relatively coarse and easily produced threads. A three-part assembly consisting of a head 1412, a sleeve 1440 and a collar 1410 is used. The head 1412 is similar to the dispenser heads in other embodiments, including those in U.S. application Ser. No. 09/614,389 in that it incorporates a perforating and flow-regulating needle 1400 along with ports in the top of the head 1413 for delivering the high pressure gas 1495 in the container as the low pressure dispensed gas 1414. The collar 1410 is screwed onto the $CO_2$ cartridge neck 1405 and selectively fixed there against rotation, e.g. by a set screw (not shown) as in the co-infusion embodiment in FIGS. 1–4. The head 1412 also is fixed against rotation by tabs 1417 that extend from the head 1412 into slots 1418 in the collar 1410, permitting axial relative motion between the head 1412 and collar 1410 but not rotational relative motion between them. A spring or gasket 1493 is situated between the head 1412 and collar 1410. The sleeve 1440 is threaded over both the head 1412 and collar 1410, bridging the space between them and thereby determining their relative axial positions.

Figure 14B:
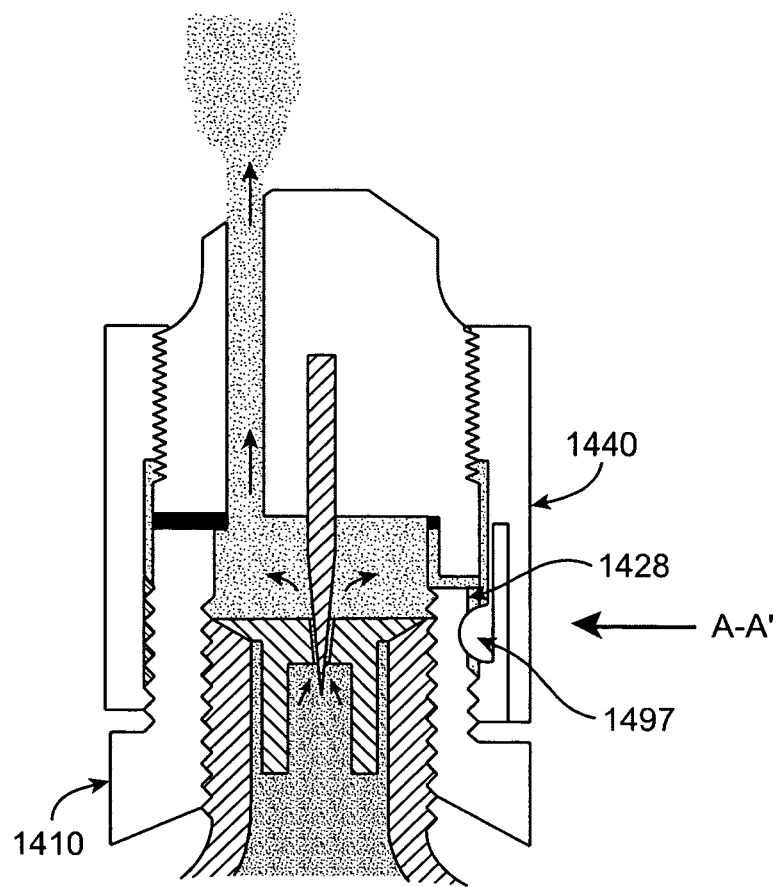
FIG. 14B shows a variation of the device of FIG. 14 including the use of an alternative detent.
Figure 14C:
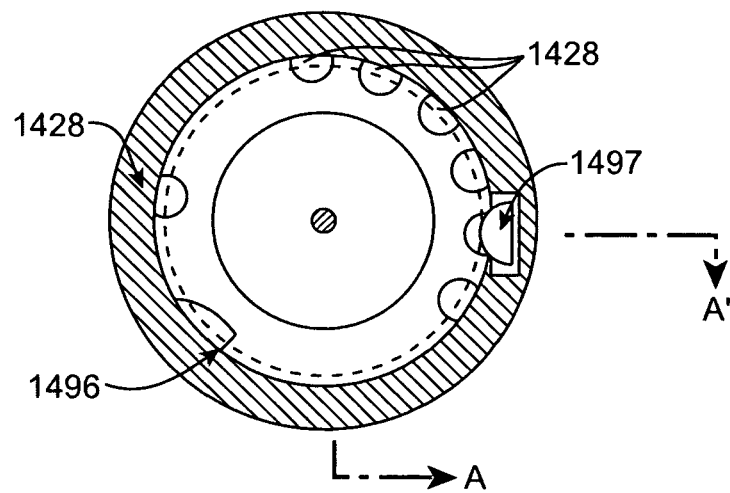
FIG. 14C shows a cross-section detail of the embodiment of FIG. 14B.

The meshing threads 1490 between the collar 1410 and the sleeve 1440 are slightly coarser than those 1491 between the head 1412 and the sleeve 1440. Thus, as the sleeve 1440 is rotated relative to the head 1412 and collar 1410, the distance between the head 1412 and the collar/cartridge assembly is changed. For example, if there are 24 threads/inch in the collar end of the sleeve and 26 threads/inch in its head end, a single turn of the sleeve relative to the head and collar/cartridge assembly advances the collar/cartridge assembly into the sleeve by $1/24$ inch but withdraws the head from the sleeve by only $1/26$ inch; therefore, the distance between the head and collar/cartridge assembly is decreased by $1/24 - 1/26 = 2/624 = 0.0032$ inch=3.2 mils, which also is the distance that the needle 1400 is advanced into the cartridge 1401 by a 360° turn of the sleeve. It can be seen that the required ~1-mil motion of the needle 1400 into and out of the cartridge orifice 1430 may be obtained with the near-optimum 120° rotation of the sleeve using easily produced coarse threads. Another advantage of the configuration in this embodiment is that a detent ball 1426 and slot 1428 arrangement 1425, including a limiting slot 1496 can be incorporated easily into the head/sleeve assembly as shown in FIG. 14 without requiring the cartridge manufacturer to produce a special slotted thread in the cartridge neck. With specific reference to FIGS. 14B–C, as an alternative, other detent arrangements, such as a pawl 1497, could also be used, and persons of ordinary skill in the art will appreciate that other alternatives are also available.

Figure 15:
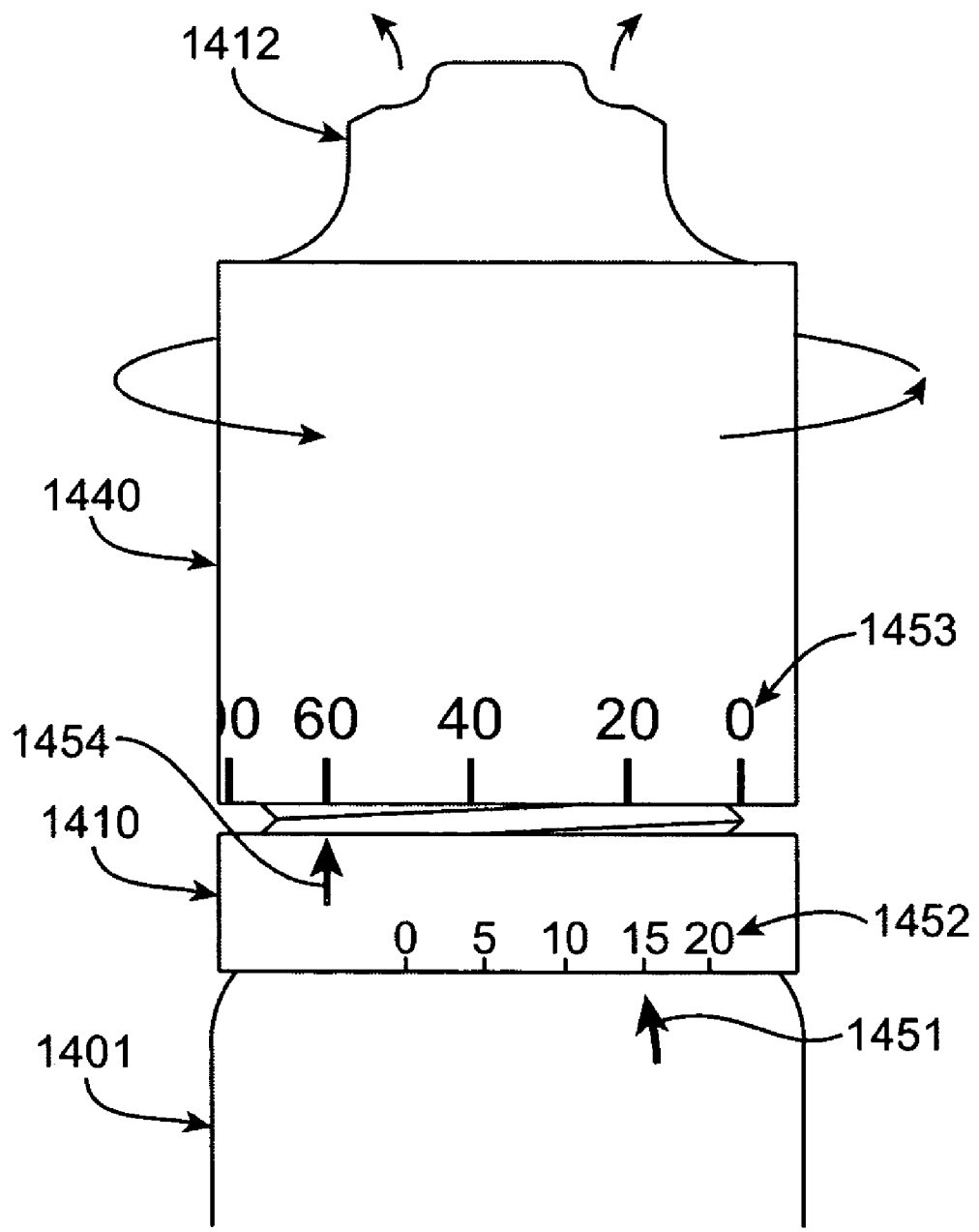
FIG. 15 shows flow rate adjustment and selection details for the embodiment of FIGS. 14A and 14C.

FIG. 15 illustrates the flow rate adjustment and selection features that may be incorporated into the embodiment of FIG. 14. The collar 1410 is fully screwed into the sleeve 1440 so that the collar arrow 1454 is at the position indicated as "0" 1453 on the sleeve 1440, and the cartridge 1401 is screwed into the collar 1410 until the tip of the needle 1400 just touches the top of the intact sealing cap 1406 (i.e. without penetrating it). The user activates the device by screwing the cartridge 1401 into the collar until the arrow 1451 on the cartridge 1401 is opposite the number on the collar 1452 that indicates the maximum flow rate that the user desires, which corresponds to the degree of seal perforation by the needle 1400 required to obtain that maximum rate. Thereafter, by rotating the sleeve 1440 the user can select the desired portion of that maximum flow delivered (which may be expressed by sleeve indicator number marks 1453 as a percent of the maximum flow) by rotating the sleeve 1440, to the corresponding sleeve indicator number 1453 position opposite the collar arrow 1454 or by counting the number of detent "clicks" corresponding to that position.

Preferred Needle Configuration

As described in U.S. application Ser. No. 09/614,389 the preferred needle configuration allows the desired very small change in the orifice area to be effected by relatively large axial displacement of the needle.

While such modification is of primary advantage when used in conjunction with the embodiments shown in U.S. application Ser. No. 09/614,389, this modification may also have advantages in the lever embodiment shown herein or in any embodiment in which it is desirable that a large displacement of the needle produce only small change in the flow.

Figure 16A:
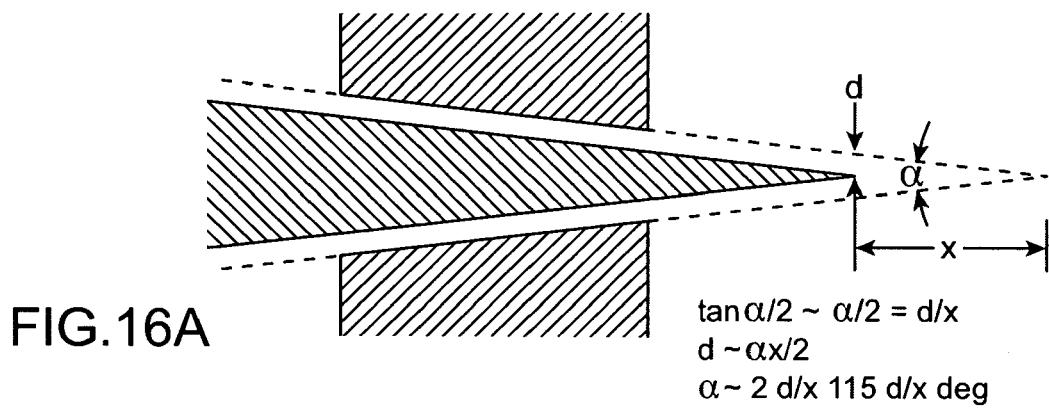
FIG. 16A illustrates the analytical relationship between the critical needle taper angle a and the size of the annular orifice d for a needle displacement x.
Figure 16C:
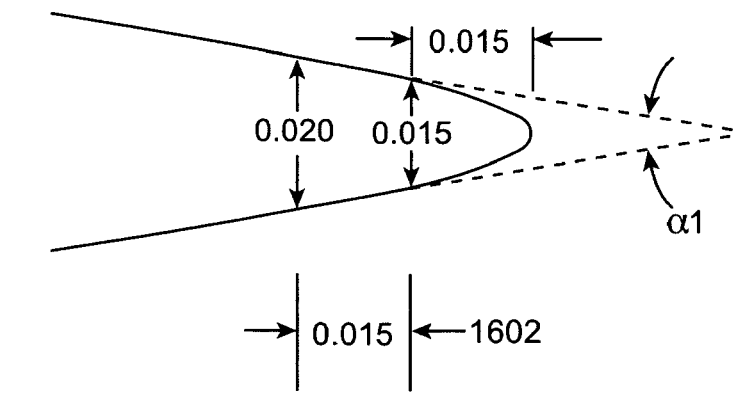
FIG. 16C is a detailed illustration of the preferred needle configuration with exemplary dimensions.
Figure 16B:
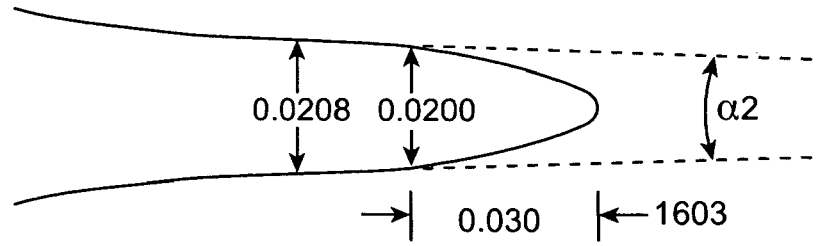
FIG. 16B is a detailed illustration of a standard needle configuration with exemplary dimensions.

An appropriate needle configuration is shown in FIG. 16C. The lowermost point of the needle 1603, over a distance approximately equal to the thickness of the cartridge seal, has essentially the same shape and size as the puncture point shown in FIG. 4A of U.S. application Ser. No. 09/614,389 and shown here in FIG. 16B. The configuration of this point is an optimum compromise between the strength of a blunt point and the reduced force requirement of a sharp point in the puncture process. However, the needle region 1602 above the point which is adjacent to the orifice formed in the cap, determines the size of the annular flow-controlling orifice when the needle is partially withdrawn. Thus, the modification of the configuration of this region of the needle may be used to obtain the required flow regulation characteristics of the dispenser.

As shown in FIG. 16A, the axial needle displacement giving a required size of the flow-controlling annular orifice is inversely dependent on the taper angle of the needle in the seat region 1602. This taper angle is approximately 20 degrees in the initial needle configuration shown in FIG. 16B, which required a displacement x of about 0.001 inch between zero flow and full flow as obtained by a 10 degree rotation of the head with 28 threads/inch. Therefore, to obtain the 120 degree optimal head rotation, the needle seat taper angle a must be about 1.7 degrees for 28 threads/inch or about 3 degrees as indicated by α2 for the preferred 48 threads/inch.

While preferred embodiments of the present invention are described above and in the following claims, it is contemplated that various modifications may be made without departing from the spirit and scope of the invention. For example, while $CO_2$ has been particularly described, other gaseous and vaporous vasodilators including NO and dilute acid vapors, as well as other physiologically active, gaseous substances (e.g., vasoactive, neuroactive, myoactive, etc.), have similar potentiating effects and are intended to be included as possible choices for substances to be co-applied with a drug for the purpose of increasing and/or controlling the effect of the drug. Furthermore, many of the features of the various embodiments described herein can be combined or added to other devices to obtain the optimum combination of features for particular applications and markets.

What is claimed is:

1. A method for controlling the effect of a drug on an individual comprising:
   administering the drug;
   generating a flow of a gaseous physiologically active agent; and
   infusing at least one facial orifice of the individual with the gaseous, physiologically active agent to enhance the action of the drug, wherein the orifice is selected from the group consisting of a nostril and a mouth, and wherein the individual substantially inhibits the passage of the gaseous physiologically active agent into the trachea and lungs by limiting inhalation of the gaseous physiologically active agent.

2. A method as in claim 1, wherein the infusing step is performed after the administering step.

3. A method as in claim 1, wherein the infusing step is performed coincident with the administering step.

4. A method as in claim 1, wherein the infusing step is performed before the administering step.

5. A method as in claim 1, wherein both a nostril and a mouth are simultaneously infused.

6. A method as in claim 1, wherein both nostrils are simultaneously infused.

7. A method as in claim 1 comprising at least one additional infusing step.

8. A method as in claim 1, further comprising the steps of:
   mixing a preselected amount of the drug and a preselected amount of the gaseous physiologically active agent to form a combination;
   wherein the generating, administering and infusing steps occur substantially simultaneously and immediately after the mixing step and the generating step further comprises generating a flow of the combination of the gaseous physiologically active agent and the drug.

9. A method as in claim 1 wherein the gaseous physiologically active agent is a gas.

10. The method of claim 1 wherein the gaseous physiologically active agent is vasoactive.

11. The method of claim 1 wherein the gaseous physiologically active agent is neuroactive.

12. The method of claim 1 wherein the gaseous physiologically active agent is myoactive.

13. A method as in claim 1, wherein the gaseous physiologically active agent is selected from the group consisting of carbon dioxide, nitric oxide, nitrous oxide, oxygen, helium, dilute mixtures of nitric oxide, and isocapnic mixtures of acid gases.

14. A method for controlling the effect of a drug on an individual having a mucous membrane, trachea and lung comprising:
   administering the drug;
   creating an environment of a gaseous physiologically active agent; and
   exposing the mucous membrane to the environment of the gaseous physiologically active agent to enhance the action of the drug, while substantially preventing the entry of the gaseous physiologically active agent into the trachea and lung, and wherein the mucous membrane is selected from the group consisting of nasal mucous membrane and oral mucous membrane.

15. A method as in claim 14, wherein the gaseous physiologically active agent is selected from the group consisting of carbon dioxide, nitric oxide, nitrous oxide, oxygen, helium, dilute mixtures of nitric oxide, and isocapnic mixtures of acid gases.

16. A method of controlling the effect of nitroglycerin for the treatment of an ailment selected from a group consisting of angina and myocardial infraction in an individual having a mucous membrane, trachea and lung, said method comprising:
  administering the nitroglycerin;
  creating an environment comprising carbon dioxide gas in a higher concentration than that found in exhaled breath;
  exposing the mucous membrane to the environment while substantially preventing the entry of the carbon dioxide gas into the trachea and lung, and wherein the mucous membrane is selected from the group consisting of nasal mucous membrane and oral mucous membrane.

17. A method of controlling the effect of a drug for the treatment of symptoms selected from a group consisting of headache and respiratory distress in an individual having a mucous membrane, trachea and lung comprising:
  administering the drug;
  creating a gaseous environment comprising $CO_2$ in a higher concentration than that found in exhaled breath;
  exposing the mucous membrane to the environment to enhance the action of the drug while substantially preventing the entry of the gaseous environment into the trachea and lung and wherein the mucous membrane is selected from the group consisting of nasal mucous membrane and oral mucous membrane.

18. A method of controlling the effect of NO in an individual having a mucous membrane, trachea and lung comprising:
  generating a flow of NO;
  infusing at least one facial orifice of the individual with the flow of NO;
  creating an environment of essentially pure carbon dioxide gas having a purity of at least 50% by volume;
  exposing the mucous membrane of the individual to the environment, wherein the mucous membrane is selected from the group consisting of nasal mucous membrane and oral mucous membrane.

19. The method of claim 18, wherein the environment comprises $CO_2$ at a purity of at least 70%.

20. The method of claim 18, wherein the environment comprises $CO_2$ at a purity of approximately 100%.

21. A method of controlling the effect of NO in an individual having a mucous membrane, trachea and lung comprising:
  generating a flow of NO;
  infusing at least one facial orifice of the individual with the flow of NO;
  creating an environment of $CO_2$ in a higher concentration than that found in exhaled breath;
  exposing the mucous membrane to the environment of $CO_2$ to enhance the action of the NO, while substantially preventing the entry of the $CO_2$ into the trachea and lung, wherein the mucous membrane is selected from the group consisting of nasal mucous membrane and oral mucous membrane.

22. A method for controlling the effect of a drug on an individual having mucous membrane comprising:
  administering the drug;
  creating a gaseous environment of essentially pure $CO_2$ having a purity of at least 50% by volume;
  exposing the mucous membrane to the environment to enhance the action of the drug, and wherein the mucous membrane is selected from the group consisting of nasal mucous membrane and oral mucous membrane, wherein the patient substantially refrains from inhalation of the $CO_2$.

23. The method of claim 22 wherein the $CO_2$ has a purity of at least 70%.

24. The method of claim 22 wherein the $CO_2$ has a purity of about 100%.

* * * * *